(12) United States Patent  
Hanscom et al.

(10) Patent No.: US 6,855,812 B2
(45) Date of Patent: Feb. 15, 2005

(54) P-GLYCOPROTEINS AND USES THEREOF

(75) Inventors: Sara Hanscom, Somerville, MA (US); Charles Crespi, Marblehead, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 28 days.

(21) Appl. No.: 10/101,433

(22) Filed: Mar. 19, 2002

(65) Prior Publication Data

US 2003/0119726 A1 Jun. 26, 2003

Related U.S. Application Data

(60) Provisional application No. 60/277,095, filed on Mar. 19, 2001.

(51) Int. Cl.$^7$ ................................................ C07K 1/00
(52) U.S. Cl. ...................................................... 530/395
(58) Field of Search ...................... 514/2, 12; 530/350, 530/395; 435/69.1, 320

(56) References Cited

U.S. PATENT DOCUMENTS

| | | | |
|---|---|---|---|
| 5,429,921 | A | 7/1995 | Harpold et al. |
| 5,641,508 | A | 6/1997 | Li et al. |
| 5,830,697 | A | 11/1998 | Sikic et al. |
| 6,617,450 | B1 | 9/2003 | Stocker et al. |
| 6,753,177 | B1 | 6/2004 | Stocker et al. |
| 2003/0119726 | A1 | 6/2003 | Hanscom et al. |

FOREIGN PATENT DOCUMENTS

| | | | | |
|---|---|---|---|---|
| WO | WO 87/05943 A | 10/1987 | | |
| WO | WO 93/02105 A | 2/1993 | | |
| WO | WO 98/13072 A | 4/1998 | | |
| WO | WO 199961589 A2 | * 12/1999 | ............ | C12N/5/10 |
| WO | WO 00/18912 A2 | 4/2000 | | |
| WO | WO 01/23565 A1 | 4/2001 | | |
| WO | WO 200123565 A1 | * 4/2001 | ....... | A61K/31/7088 |

OTHER PUBLICATIONS

Puel et al. Database Genbank Accession No. AAC02113. National Library of Medicine, Bethesda, MD, Jan. 28, 1998.*
Ng et al., "Identification of Members of the P–Glycoprotein Multigene Family," *Molecular and Cellular Biology*, Mar. 1989, vol. 9, No. 3, pp. 1224–1232.
Gant et al., "In Vivo Induction of Liver P–Glycoprotein Expression by Xenobiotics in Monkeys," *Toxicology and Applied Pharmacology*, 1995, vol. 133, pp. 269–276.
Chen et al., "Genomic Organization of the Human Multidrug Resistance (MDR1) Gene and Origin of P–glycoproteins," *The Journal of Biological Chemistry*, Jan. 5, 1990, vol. 265, No. 1, pp. 506–514.
GenBank accession No. AF045016.
GenBank accession No. AF092810.
Genbank accession No. M14758.
Genbank accession No. AF016535.
Genbank accession No. NM_000927.
Sharom et al., "Interaction of the P–Glycoprotein Multidrug Transporter (MDR1) with High Affinity Peptide Chemosensitizers in Isolated Membranes, Reconstructed Systems, and Intact Cells," *Biochem. Pharmacol.*, 1999, vol. 58, pp. 571–586.
Sugden et al., "A Vector That Replicates as a Plasmid and can be Efficiently Selected in B–Lymphoblasts Transformed by Epstein–Barr Virus," *Mol. Cell Biol.* 1985, vol. 5, No. 2, pp. 410–413.
Yates et al., "Stable Replication of Plasmids Derived from Epstein–Barr Virus in Various Mammalian Cells," *Nature (Lond.)* 1985, vol. 313, pp. 812–815.
Sarkadi et al., "Expression of the Human Multidrug Resistance cDNA in Insect Cells Generates a High Activity Drug–stimulated Membrane ATPase," *J. Biol. Chem.* 1992, vol. 267, pp. 4854–4858.
Druekes et al., "Photometric Microtiter Assay of Inorganic Phosphate in the Presence of Acid–Labile Organic Phosphates," *Anal. Biochem.* 1995 vol. 230, pp. 173–177.
Steingold et al., "Characterization of Canine *MDR1* mRNA: Its Abundance in Drug Resistant Cell Lines and in Vivo," *Anticancer Res.* 1998, vol. 18, pp. 393–400.
Yang et al., "Progesterone Interacts with P–Glycoprotein in Multi–resistant Cells and in the Endometrium of Gravid Uterus," *J. of Biol Chem.* 1989, vol. 264, No. 2, pp. 782–788.
Chen et al., Multidrug–resistant Human Sarcoma Cells with Mutant P–Glycoprotein, Altered Phenotype, and Resistance to Cyclosporins, *J. of Biol. Chem.* 1989, vol. 272, No. 9, pp. 5974–5982.
Chen et al., "Internal Duplication and homology with Bacterial Transport Proteins in the mdr1 (P–Glycoprotein) Gene from Multidrug–Resistant Human Cells," *Cell, 1986*, vol. 47, pp. 381–389.

(List continued on next page.)

Primary Examiner—Jon Weber
Assistant Examiner—Sheridan Snedden
(74) Attorney, Agent, or Firm—Wolf, Greenfield & Sacks, P.C.

(57) ABSTRACT

The invention pertains to rhesus monkey P-glycoproteins and related P-glycoproteins which include rhesus-specific amino acids, as well as nucleic acids which encode those polypeptides. The present invention also includes fragments and biologically functional variants of the rhesus monkey P-glycoprotein. The invention further relates to methods of using such rhesus monkey P-glycoprotein nucleic acids and polypeptides, especially in methods for determining bioavailability of drugs and for screening for inhibitors of rhesus PGP. Also included are rhesus PGP inhibitors which inhibit rhesus PGP activity by inhibiting the expression or function of rhesus PGP.

6 Claims, No Drawings

OTHER PUBLICATIONS

Ambudkar et al., Relation Between the Turnover Number for Vinblastine Transport and for Vinblastine–stimulated ATP Hydrolysis By Human P–Glycoprotein),*J. of Biolo. Chem.*, 1997, vol. 272, No. 34, pp: 21160–21166.

Kioka et al., "P–Glycoprotein Gene (MDR1) cDNA from Human Adrenal: Normal P–Glycoprotein Carries $GLY^{185}$ with an Altered Pattern of Multidrug Resistance," *Biochem. and Biophys. Res. Comm.*, 1989, vol. 162, No. 1, pp. 224–231.

Ma et al., Molecular Cloning, Expression and Function Characterization of the Canine Multidrug Resistance Protein (MRP1), *Proc. of the Amer. Assoc. for Cancer Res. Ann.*, 2000, vol. 41, p. 765.

Capella et al., "Expression of Functionally P–Glycoprotein in MA104 Kidney Cells," *Zeitschrift Naturforsch.* 1999, vol. 54c, p. 119–127.

Schrenk et al., "Induction of Multidrug Resistance Gene Expression During Cholestasis in rats and Nonhuman Primates," *Hepatology 1993*,vol. 17, pp. 854–860.

Motomura et al., "Inhibition of P–Glycoprotein and Recovery of Drug Sensitivity of Human Acute Leukemic Blast Cells by Multidrug Resistance Gene (mdr1) Antisense Oligonucleotides," *Blood*, 1998, vol. 91, No. 9, pp. 3163–3171.

Romagnoli et al., "Exitope Mapping of the Monoclonal Antibody MM12.10 to External MDR1 P–Glycoprotein Domain by Synthetic Peptide Scanning and Phage Display Technologies," *Biol. Chem.*, 1999, vol. 380, pp. 553–559.

Fox et al., "Heterologous Expression of and the Development of Assays for Interaction of Drugs with Human P–Glycoprotein," *Drug Metab. Revs.*, 2000, vol. 32(Supp 1), p. 41 (ABSTRACT).

International Search Report in PCT Application No. PCT/US02/08325, mailed Aug. 13, 2003.

International Preliminary Examination Report in PCT Application No. PCT/US02/08325, mailed Jun. 25, 2004.

* cited by examiner

P-GLYCOPROTEINS AND USES THEREOF

RELATED APPLICATIONS

This application claims priority under 35 U.S.C. § 119 to U.S. provisional application Ser. No. 60/277,095 filed on Mar. 19, 2001.

FIELD OF THE INVENTION

The invention pertains to P-glycoproteins of rhesus monkey (*Macaca mulatta*).

BACKGROUND OF THE INVENTION

P-Glycoprotein (PGP; also known as multidrug transporter, MDR1) is a member of the ABC transporter superfamily and is expressed in the human intestine, liver and other tissues. This enzyme serves as an efflux pump exporting small molecules across the cell membrane. It has been known for several years that high level expression of PGP is a mechanism for tumor resistance to cancer chemotherapy. Intestinal expression of PGP may affect the oral bioavailability of drug molecules that are substrates for this transporter. PGP can efficiently efflux drugs back into the intestinal lumen and thus reduce the amount of drug that enters into circulation.

The measurement of interaction with PGP can provide a better understanding of the reasons why particular drugs demonstrate low or high bioavailability. Interaction with PGP can be studied using either direct assays of drug transport in polarized cell systems or with indirect assays such as drug-stimulated ATPase activity and inhibition of the transport of fluorescent substrates.

Therefore there is a need for additional PGP polypeptides, preferably which are closely related to the human PGP, for use in the foregoing drug assays.

SUMMARY OF THE INVENTION

Nucleic acids encoding the P-glycoprotein of rhesus monkey (*Macaca mulatta*) have now been identified, isolated, cloned and sequenced. This PGP is closely related (has a high degree of identity) to the cynomologous monkey, human, and dog PGPs. The invention provides isolated nucleic acid molecules, nucleic acid molecules comprising nucleotide deletions, additions, substitutions or unique fragments of those molecules, expression vectors containing the foregoing, and host cells transfected with those molecules. The invention also provides isolated polypeptides and inhibitors of the foregoing nucleic acids and polypeptides which reduce drug transport. The PGP nucleic acids and polypeptides are useful in assays for evaluating bioavailability of drugs, as well as for the optimization or discovery of drugs. In addition, the foregoing can be used in the diagnosis or treatment of conditions characterized by PGP activity and can be used in methods in which it is therapeutically useful to increase or decrease PGP activity.

According to one aspect of the invention, isolated nucleic acid molecules are provided. The nucleic acid molecules are selected from the group consisting of (a) nucleic acid molecules that hybridize under stringent conditions to the nucleotide sequence of SEQ ID NO:1, wherein said nucleic acid encodes a rhesus P-glycoprotein (b) nucleic acid molecules that code for the amino acid sequence of SEQ ID NO:2 (c) degenerate nucleic acids that differ from the biologically isolated nucleic acids in codon sequence due to the degeneracy of the genetic code and (d) complements of (a) (b) or (c). In certain embodiments, the isolated nucleic acid molecule codes for SEQ ID NO:2. In other embodiments, the isolated nucleic acid molecule comprises the nucleotide sequence of SEQ ID NO:1.

Also provided are isolated nucleic acid molecules that are at least 85% identical to SEQ ID NO:1. In preferred embodiments, the nucleic acids are at least about 86, 87, 88, 89, 90, 91, 92, 93, 94, 95, 96, 97, 98, 99, or 99.5% identical to SEQ ID NO:1. Isolated polypeptides that are at least about 90, 91, 92, 93, 94, 95, 96, 97, 98, 99, or 99.5% identical to SEQ ID NO:2 also are provided.

According to another aspect of the invention, isolated P-glycoprotein polypeptides or fragments thereof are provided which include at least one amino acid of a rhesus P-glycoprotein selected from the group consisting of amino acids 55, 93, 94, 95, 230 and 234 of SEQ ID NO:2 wherein the P-glycoprotein is identical to a cynomologous P-glycoprotein except for the at least one amino acid of a rhesus P-glycoprotein. In certain embodiments, the cynomologous P-glycoprotein is selected from the group of SEQ ID NO:3 and SEQ ID NO:4.

According to yet another aspect of the invention, isolated P-glycoprotein polypeptides or fragments thereof which include at least one amino acid of a rhesus P-glycoprotein selected from the group consisting of amino acids 12, 24, 30, 55, 74, 78, 86, 89, 90, 91, 92, 93, 94, 95, 98, 100, 102, 105, 106, 107, 188, 230, 234, 327, 339, 366, 497, 521, 638, 653, 659, 662, 680, 733, 741, 745, 748, 764, 768, 838, 854, 924, 970, 1006, 1030, 1041, 1051, 1106, 1131, 1171 and 1280 of SEQ ID NO:2 wherein the P-glycoprotein is identical to a human P-glycoprotein except for the at least one amino acid of a rhesus P-glycoprotein. In some embodiments, the human P-glycoprotein is selected from the group of SEQ ID NO:5 and SEQ ID NO:6.

According to yet another aspect of the invention, isolated P-glycoprotein polypeptides or fragments thereof which include at least one amino acid of a rhesus P-glycoprotein selected from the group consisting of amino acids 3, 6, 8, 10, 14, 15, 16, 17, 18, 19, 20, 21, 22, 23, 25, 26, 28, 29, 30, 31, 36, 38, 48, 52, 55, 56, 64, 74, 78, 84, 85, 86, 87, 88, 89, 90, 91, 92, 93, 94, 96, 97, 98, 99, 101, 103, 104, 105, 106, 107, 108, 109, 113, 116, 148, 193, 198, 200, 213, 230, 234, 289 322, 327, 330, 348, 366, 398, 451, 455, 456, 468, 473, 497, 521, 533, 634, 644, 645, 651, 653, 658, 659, 667, 668, 675, 676, 677, 678, 686, 690, 692, 694, 695, 697, 704, 708, 718, 732, 733, 737, 745, 746, 748, 757, 760, 768, 838, 915, 921, 924, 943, 944, 947, 969, 970, 971, 973, 975, 984, 1011, 1018, 1026, 1027, 1051, 1096, 1099, 1106, 1131, 1145, 1149, 1150, 1159, 1163, 1166, 1169, 1253, 1271, and 1274 of SEQ ID NO:2 and wherein the P-glycoprotein is identical to a dog P-glycoprotein except for the at least one amino acid of a rhesus P-glycoprotein. In some embodiments, the dog P-glycoprotein is selected from the group of SEQ ID NO:7, SEQ ID NO:8, SEQ ID NO:9, SEQ ID NO: 10, and SEQ ID NO: 11.

In preferred embodiments, the isolated P-glycoprotein polypeptides or fragments thereof include an amino acid sequence selected from the group consisting of SEQ ID NO:2, fragments of SEQ ID NO:2. Yet other polypeptides include combinations of the foregoing dog, human, cynomologous and rhesus PGP polypeptides.

According to still other embodiments of the invention, isolated nucleic acid molecules are provided which encode the foregoing isolated P-glycoprotein polypeptides or fragments thereof. Also included expression vectors comprising the foregoing isolated nucleic acid molecules operably linked to a promoter, as well as host cells transformed or transfected with the expression vectors.

In another aspect of the invention, agents which selectively bind the isolated PGP polypeptides are provided. Preferably the agent does not bind a cynomologous, human or dog P-glycoprotein, except those provided herein. In certain embodiments, the agent is a polypeptide preferably one selected from the group consisting of monoclonal antibodies, polyclonal antibodies, Fab antibody fragments, $F(ab)_2$ antibody fragments and antibody fragments including a CDR3 region. Also provided are agents which selectively bind the foregoing isolated nucleic acid molecules, preferably antisense nucleic acid molecules which selectively bind to the isolated nucleic acid molecule.

According to another aspect of the invention, methods for predicting the bioavailability of a compound are provided. The methods include measuring the transmembrane transport of a test compound by a first P-glycoprotein, comparing the transmembrane transport of the test compound by the first P-glycoprotein and a second P-glycoprotein to predict the bioavailability of the test compound, wherein the relative amount or rate of transport by the first P-glycoprotein and the second P-glycoprotein is predictive of bioavailability of the test compound. In certain embodiments the first P-glycoprotein is selected from the group consisting of dog P-glycoproteins and primate P-glycoproteins, preferably one of the foregoing polypeptides. In other embodiments the second P-glycoprotein is a human P-glycoprotein.

In still other aspects of the invention, methods for inhibiting P-glycoprotein transporter activity in a mammalian cell are provided. The methods include contacting the mammalian cell with an amount of one of the foregoing agents effective to inhibit P-glycoprotein transporter activity in the mammalian cell.

Also included in the invention are methods for increasing bioavailability of a drug in a subject. The methods include administering to a subject in need of such treatment one of the foregoing agents in an amount effective to increase bioavailability of a drug. The inhibitor can be administered prior to administering the drug, or concurrently with the drug.

Also provided are methods for increasing P-glycoprotein transporter activity in a cell. These methods include contacting the cell with a molecule selected from the group consisting of the foregoing nucleic acid molecules, in an amount effective to increase P-glycoprotein transporter activity in the cell. The cell can be contacted under conditions whereby the P-glycoprotein is expressed.

According to yet another aspect of the invention, methods for identifying lead compounds for a pharmacological agent useful in the treatment of disease associated with P-glycoprotein transporter activity are provided. The methods include providing a cell or other membrane-encapsulated space comprising a P-glycoprotein as provided herein; contacting the cell or other membrane-encapsulated space with a candidate pharmacological agent under conditions which, in the absence of the candidate pharmacological agent, cause a first amount of P-glycoprotein transporter activity; and determining a second amount of P-glycoprotein transporter activity as a measure of the effect of the pharmacological agent on the P-glycoprotein transporter activity, wherein a second amount of P-glycoprotein transporter activity which is less than the first amount indicates that the candidate pharmacological agent is a lead compound for a pharmacological agent which reduces P-glycoprotein transporter activity and wherein a second amount of P-glycoprotein transporter activity which is greater than the first amount indicates that the candidate pharmacological agent is a lead compound for a pharmacological agent which increases P-glycoprotein transporter activity. The methods can further include a step of loading the cell or other membrane-encapsulated space with a detectable compound, wherein the compound is detected as a measure of the P-glycoprotein transporter activity.

Also included are methods for identifying compounds which selectively bind a P-glycoprotein. The methods include contacting a P-glycoprotein provided herein with a compound, and determining the binding of the compound to the P-glycoprotein. The methods can further include determining the effect of the compound on the P-glycoprotein transporter activity of the P-glycoprotein or determining the effect of the compound on the ATPase activity of the P-glycoprotein.

Additional methods provided according to the invention include methods for determining ATPase activity of a P-glycoprotein. The methods include contacting a host cell as provided above, or a membrane fraction thereof, with a test drug, and measuring ATPase activity of the P-glycoprotein. In certain embodiments, the step of measuring ATPase activity is performed at least twice at different times. Also provided methods for determining transmembrane transport of a compound by a P-glycoprotein. The methods include contacting a host cell provided above, or a membrane fraction thereof, with a test drug, and measuring transport of the test drug under sink conditions in at least one direction of transport selected from the group consisting of the apical to basolateral direction and the basolateral to apical direction. In certain embodiments the step of measuring transport of the test drug is performed at least twice at different times.

These and other aspects of the invention are described in greater detail below.

DETAILED DESCRIPTION OF THE INVENTION

The present invention in one aspect involves the identification of cDNAs encoding rhesus monkey (*Macaca mulatta*) P-glycoproteins, referred to herein as rhesus PGP. The nucleotide sequence of the rhesus PGP is presented as SEQ ID NO:1, and the amino acid sequence of the rhesus PGP is presented as SEQ ID NO:2. Surprisingly, whereas much of the polypeptide presented herein is identical to cynomologous PGP, rhesus PGP has several single amino acid differences. This species difference in the very highly conserved protein domains of the P-glycoprotein is entirely unexpected.

The invention involves in one aspect rhesus PGP nucleic acids and polypeptides, as well as therapeutics relating thereto. The invention also embraces isolated functionally equivalent variants, useful analogs and fragments of the foregoing nucleic acids and polypeptides; complements of the foregoing nucleic acids; and molecules which selectively bind the foregoing nucleic acids and polypeptides.

The rhesus PGP nucleic acids and polypeptides of the invention are isolated. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

As used herein a rhesus PGP nucleic acid refers to an isolated nucleic acid molecule which codes for a rhesus PGP polypeptide. Such nucleic acid molecules code for rhesus PGP polypeptides which include the sequence of SEQ ID NO:2 and fragments thereof. The nucleic acid molecules include the nucleotide sequences of SEQ ID NO:1, and nucleotide sequences which differ from the sequences of SEQ ID NO:1 in codon sequence due to the degeneracy of the genetic code. The rhesus PGP nucleic acids of the invention also include alleles of the foregoing nucleic acids, as well as fragments of the foregoing nucleic acids. Such fragments can be used, for example, as probes in hybridization assays and as primers in a polymerase chain reaction (PCR). Preferred rhesus PGP nucleic acids include the nucleic acid sequence of SEQ ID NO:1. Complements of the foregoing nucleic acids also are embraced by the invention.

As used herein "rhesus PGP activity" refers to an ability of a PGP polypeptide to export small molecules across the cell membrane. A molecule which inhibits rhesus PGP activity (an antagonist) is one which inhibits export of small molecules via PGP and a molecule which increases rhesus PGP activity (an agonist) is one which increases export of small molecules via PGP. Changes in rhesus PGP activity can be measured by assays such as those disclosed herein, including efflux of fluorescent compounds from cells.

Alleles of the rhesus PGP nucleic acids of the invention can be identified by conventional techniques. For example, alleles of rhesus PGP can be isolated by hybridizing a probe which includes at least a fragment of SEQ ID NO:1 under stringent conditions with a cDNA library and selecting positive clones. Thus, an aspect of the invention is those nucleic acid sequences which code for rhesus PGP polypeptides and which hybridize to a nucleic acid molecule consisting of SEQ ID NO:1 under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH 7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the DNA is transferred is washed at 2×SSC at room temperature and then at 0.1–0.5×SSC/0.1× SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of rhesus PGP nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 85% nucleotide identity and/or at least 90% amino acid identity to the sequences of PGP nucleic acid and polypeptides, respectively, in some instances will share at least 90% nucleotide identity and/or at least 95% amino acid identity and in still other instances will share at least 95% nucleotide identity and/or at least 99% amino acid identity and in still yet other instances will share at least 99% nucleotide identity and/or at least 99.5% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov, using default settings. Pairwise and ClustalW alignments (BLOSUM30 matrix setting) as well as Kyte-Doolittle hydropathic analysis can be obtained using the MacVector sequence analysis software (Oxford Molecular Group, Hunt Valley, Md.). Watson-Crick complements of the foregoing nucleic acids also are embraced by the invention.

In screening for rhesus PGP nucleic acids, a Southern blot may be performed using the foregoing stringent conditions, together with a radioactive probe. After washing the membrane to which the DNA is finally transferred, the membrane can be placed against X-ray film to detect the radioactive signal.

The rhesus PGP nucleic acids of the invention also include degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating rhesus PGP polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as transporter activity, etc. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention also provides isolated fragments of SEQ ID NO:1. The fragments can be used as probes in Southern blot assays to identify such nucleic acids, or can be used in amplification assays such as those employing PCR. Smaller fragments are those comprising 12, 13, 14, 15, 16, 17, 18, 20, 22, 25, 30, 40, 50, or 75 nucleotides, and every integer therebetween, and are useful e.g. as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the rhesus PGP polypeptides, useful, for example, in the preparation of antibodies, in immunoassays, and the like. The foregoing nucleic acid fragments further can be used as antisense molecules to inhibit the expression of rhesus PGP nucleic acids and polypeptides, particularly for therapeutic purposes as described in greater detail below.

The invention also includes functionally equivalent variants of the rhesus PGP, which include variant nucleic acids and polypeptides which retain one or more of the functional properties of the rhesus PGP. Preferably such variants include the rhesus-specific N-terminal domain (e.g., amino acids 86–107 of SEQ ID NO:2). For example, variants include a fusion protein which includes the extracellular and transmembrane domains of the rhesus PGP which retains the ability to transport molecules. Still other functionally equivalent variants include truncations, deletions, point mutations, or additions of amino acids to the sequence of SEQ ID NO:2 which retain functions of SEQ ID NO:2. Functionally equivalent variants also include a rhesus PGP which has had a portion of the N-terminus removed or replaced by a similar domain from another P-glycoprotein (e.g. a "domain-swapping" variant). Other functionally equivalent variants will be known to one of ordinary skill in the art, as will methods for preparing such variants. The activity of a functionally equivalent variant can be determined using the methods provided herein, and in references that have described assays using P-glycoproteins of other species. Such variants are useful, inter alia, for evaluating bioavailability of drugs, in assays for identification of compounds which bind and/or regulate the transporter function of the rhesus PGP, and for determining the portions of the rhesus PGP which are required for transporter activity.

Variants which are non-functional also can be prepared as described above. Such variants are useful, for example, as negative controls in experiments testing transporter activity.

A rhesus PGP nucleic acid, in one embodiment, is operably linked to a gene expression sequence which directs the expression of the rhesus PGP nucleic acid within a eukaryotic or prokaryotic cell. The "gene expression sequence" is any regulatory nucleotide sequence, such as a promoter sequence or promoter-enhancer combination, which facilitates the efficient transcription and translation of the rhesus PGP nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney murine leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined rhesus PGP nucleic acid. The gene expression sequences optionally includes enhancer sequences or upstream activator sequences as desired.

The rhesus PGP nucleic acid sequence and the gene expression sequence are said to be "operably linked" when they are covalently linked in such a way as to place the transcription and/or translation of the rhesus PGP coding sequence under the influence or control of the gene expression sequence. If it is desired that the rhesus PGP sequence be translated into a functional protein, two DNA sequences are said to be operably linked if induction of a promoter in the 5' gene expression sequence results in the transcription of the rhesus PGP sequence and if the nature of the linkage between the two DNA sequences does not (1) result in the introduction of a frame-shift mutation, (2) interfere with the ability of the promoter region to direct the transcription of the rhesus PGP sequence, or (3) interfere with the ability of the corresponding RNA transcript to be translated into a protein. Thus, a gene expression sequence would be operably linked to a rhesus PGP nucleic acid sequence if the gene expression sequence were capable of effecting transcription of that rhesus PGP nucleic acid sequence such that the resulting transcript might be translated into the desired protein or polypeptide.

The rhesus PGP nucleic acid molecules and the rhesus PGP polypeptides (including the rhesus PGP inhibitors described below) of the invention can be delivered to the eukaryotic or prokaryotic cell alone or in association with a vector. In its broadest sense, a "vector" is any vehicle capable of facilitating: (1) delivery of a rhesus PGP nucleic acid or polypeptide to a target cell, (2) uptake of a rhesus PGP nucleic acid or polypeptide by a target cell, or (3) expression of a rhesus PGP nucleic acid molecule or polypeptide in a target cell. Preferably, the vectors transport the rhesus PGP nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor (e.g. a receptor, an antigen recognized by an antibody) for the targeting ligand. In this manner, the vector (containing a rhesus PGP nucleic acid or a rhesus PGP polypeptide) can be selectively delivered to a specific cell. In general, the vectors useful in the invention are divided into two classes: biological vectors and chemical/physical vectors. Biological vectors are more useful for delivery/uptake of rhesus PGP nucleic acids to/by a target cell. Chemical/physical vectors are more useful for delivery/uptake of rhesus PGP nucleic acids or rhesus PGP proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be linked to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenoviruses; adeno-associated virus; SV40-type viruses; polyoma viruses; poxviruses; retroviruses; Epstein-Barr virus; papilloma viruses; herpes virus; vaccinia virus; and polio virus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual*," W. H. Freeman C. O., New York (1990) and Murry, E. J. Ed. "*Methods in Molecular Biology*," vol. 7, Humana Press, Inc., Clifton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a rhesus PGP polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV or pcDNA1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficient transcription in vitro. The plasmid is described by Mishizuma and Nagata (*Nuc. Acids Res.* 18:5322, 1990), and its use in transfection experiments is disclosed by, for example, Demoulin (*Mol Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992).

In addition to the biological vectors, chemical/physical vectors may be used to deliver a rhesus PGP nucleic acid or polypeptide to a target cell and facilitate uptake thereby. As used herein, a "chemical/physical vector" refers to a natural or synthetic molecule, other than those derived from bacteriological or viral sources, capable of delivering the isolated rhesus PGP nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as a delivery vector in vivo or in vitro. It has been shown that large unilamellar vesicles (LUV), which range in size from 0.2–4.0μ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the rhesus PGP nucleic acid to the nucleus of the host cell.

Liposomes are commercially available from (Gibco BRL, Carlsbad, Calif.), for example, as LIPOFECTIN™ and LIPOFECTACE™, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications.

Other exemplary compositions that can be used to facilitate uptake by a target cell of the rhesus PGP nucleic acids include calcium phosphate and other chemical mediators of intracellular transport, microinjection compositions, electroporation and homologous recombination compositions (e.g., for integrating a rhesus PGP nucleic acid into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of the rhesus PGP cDNA sequences in expression vectors, as well as to transfect host cells and cell lines, be these prokaryotic (e.g., *E. coli*), or eukaryotic (e.g., COS cells, yeast expression systems and recombinant baculovirus expression in insect cells). Especially useful are mammalian cells such as human, pig, goat, primate, etc. They may be of a wide variety of tissue types, and include primary cells and cell lines. Specific examples include intestinal cells and liver cells. The expression vectors require that the pertinent sequence, i.e., those nucleic acids described supra, be operably linked to a promoter.

The invention also provides isolated rhesus PGP polypeptides which include the amino acid sequences of SEQ ID NO:2 and fragments thereof, encoded by the rhesus PGP nucleic acids described above. Rhesus PGP polypeptides also embrace alleles, functionally equivalent variants and analogs (those non-allelic polypeptides which vary in amino acid sequence from the disclosed rhesus PGP polypeptides by 1, 2, 3, 4, 5, or more amino acids) provided that such polypeptides retain rhesus PGP activity. Non-functional variants also are embraced by the invention; these are useful as antagonists of transporter function, as negative controls in assays, and the like. Such alleles, variants, analogs and fragments are useful, for example, alone or as fusion proteins for a variety of purposes including as a component of assays.

Fragments of a polypeptide preferably are those fragments which retain a distinct functional capability of the rhesus PGP polypeptide, in particular as a transporter of various molecules. Other functional capabilities which can be retained in a fragment of a rhesus PGP polypeptide include interaction with antibodies and interaction with other polypeptides (such as would be found in a protein complex). Those skilled in the art are well versed in methods for selecting fragments which retain a functional capability of the rhesus PGP. Confirmation of the functional capability of the fragment can be carried out by synthesis of the fragment and testing of the capability according to standard methods. For example, to test the transporter activity of a rhesus PGP fragment, one inserts or expresses the fragment in a cell in which molecular transport can be measured. Such methods, which are standard in the art, are described further herein.

The invention embraces variants of the rhesus PGP polypeptides described above. As used herein, a "variant" of a rhesus PGP polypeptide is a polypeptide which contains one or more modifications to the primary amino acid sequence of a rhesus PGP polypeptide. Modifications which create a rhesus PGP variant can be made to a rhesus PGP polypeptide for a variety of reasons, including 1) to reduce or eliminate an activity of a rhesus PGP polypeptide, such as transport; 2) to enhance a property of a rhesus PGP polypeptide, such as protein stability in an expression system or the stability of protein-protein binding; 3) to provide a novel activity or property to a rhesus PGP polypeptide, such as addition of an antigenic epitope or addition of a detectable moiety; or 4) to establish that an amino acid substitution does or does not affect molecular transport activity. Modifications to a rhesus PGP polypeptide are typically made to the nucleic acid which encodes the rhesus PGP polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the rhesus PGP amino acid sequence. One of skill in the art will be familiar with methods for predicting the effect on protein conformation of a change in protein sequence, and can thus "design" a variant rhesus PGP according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a rhesus PGP polypeptide can be proposed and tested to determine whether the variant retains a desired conformation.

Variants include rhesus PGP polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a rhesus PGP polypeptide by eliminating proteolysis by proteases in an expression system (e.g., dibasic amino acid residues in yeast expression systems in which KEX2 protease activity is present).

Mutations of a nucleic acid which encode a rhesus PGP polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant rhesus PGP polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a rhesus PGP gene or cDNA clone to enhance expression of the polypeptide.

The activity of variants of rhesus PGP polypeptides can be tested by cloning the gene encoding the variant rhesus PGP polypeptide into a bacterial or mammalian expression vector, introducing the vector into an appropriate host cell, expressing the variant rhesus PGP polypeptide, and testing for a functional capability of the rhesus PGP polypeptides as disclosed herein. For example, the variant rhesus PGP polypeptide can be tested for ability to provide molecular transport (e.g., efflux), as set forth below in the examples. Preparation of other variant polypeptides may favor testing of other activities, as will be known to one of ordinary skill in the art.

The skilled artisan will also realize that conservative amino acid substitutions may be made in rhesus PGP polypeptides to provide functionally equivalent variants of the foregoing polypeptides, i.e, variants which retain the functional capabilities of the rhesus PGP polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the rhesus PGP polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of rhesus PGP polypeptide to produce functionally equivalent variants of rhesus PGP typically are made by alteration of the nucleic acid sequence encoding rhesus PGP polypeptides (e.g., SEQ ID NO:1). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a rhesus PGP polypeptide. The activity of functionally equivalent fragments of rhesus PGP polypeptides can be tested by cloning the gene encoding the altered rhesus PGP polypeptide into a bacterial or mammalian expression vector, introducing the vector into an appropriate host cell, expressing the altered rhesus PGP polypeptide, and testing for the ability of the rhesus PGP polypeptide to mediate transmembrane transport of compounds. Peptides which are chemically synthesized can be tested directly for function.

A variety of methodologies well-known to the skilled practitioner can be utilized to obtain isolated rhesus PGP molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating rhesus PGP polypeptides. These include, but are not limited to, immunochromatography, HPLC, size-exclusion chromatography, ion-exchange chromatography and immune-affinity chromatography.

The invention as described herein has a number of uses, some of which are described elsewhere herein. For example, the invention permits isolation of the rhesus PGP polypeptide molecules by e.g., expression of a recombinant nucleic acid to produce large quantities of polypeptide which may be isolated using standard protocols. As another example, the isolation of the rhesus PGP gene makes it possible for rhesus PGP to be used in methods for assaying of molecular transport, such as drug bioavailability studies. These methods involve determining transport of a drug by a first species' PGP (e.g., rhesus) in comparison to transport of the drug by other species' PGP (e.g. human) as a method for determining or predicting the bioavailability of the drug. Thus the results of whole animal studies on the metabolism of a drug can be evaluated in view of the relative rates or amounts of P-glycoprotein transport of the drug. For example, if a drug administered to a dog has good oral bioavailability and low transport by dog PGP, one can predict that the oral bioavailability of the drug in humans will be good if the transport by human PGP is also low. Conversely, if the transport of the drug by human PGP is high, then the bioavailability of the drug would be predicted to be low.

The invention also embraces agents which bind selectively to the rhesus PGP nucleic acid molecules or polypeptides as well as agents which bind to variants and fragments of the polypeptides and nucleic acids as described herein. The agents include polypeptides which bind to rhesus PGP, and antisense nucleic acids, both of which are described in greater detail below. The agents can inhibit or increase rhesus PGP activity (antagonists and agonists, respectively).

Some of the agents are inhibitors. A rhesus PGP inhibitor is an agent that inhibits rhesus PGP mediated transport of molecules across a cell membrane. Efflux assays can be performed to screen and/or determine whether a rhesus PGP inhibitor has the ability to inhibit rhesus PGP activity, and whether the inhibition is selective. An exemplary assay of efflux is described below in the Examples.

In one embodiment the rhesus PGP inhibitor is an antisense oligonucleotide that selectively binds to a rhesus PGP nucleic acid molecule, to reduce the expression of rhesus PGP (or other species' PGPs) in a cell. This is desirable in virtually any medical condition wherein a reduction of PGP transporter activity is desirable, e.g., to increase retention of cytotoxic agents in a cell.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol Neurobiol.* 14(5):439–457, 1994) and at which polypeptides are not expected to bind. Thus, the present invention also provides for antisense oligonucleotides which are complementary to allelic or homologous cDNAs and genomic DNAs corresponding to rhesus PGP nucleic acid containing SEQ ID NO:1.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding rhesus PGP polypeptides, together with pharmaceutically acceptable carriers.

Agents which bind rhesus PGP also include binding peptides and other molecules which bind to the rhesus PGP polypeptide and complexes containing the rhesus PGP polypeptide. When the binding molecules are inhibitors, the molecules bind to and inhibit the activity of rhesus PGP. To determine whether a rhesus PGP binding agent binds to rhesus PGP any known binding assay may be employed. For example, the binding agent may be immobilized on a surface and then contacted with a labeled rhesus PGP polypeptide. The amount of rhesus PGP which interacts with the rhesus PGP binding agent or the amount which does not bind to the rhesus PGP binding agent may then be quantitated to determine whether the rhesus PGP binding agent binds to rhesus PGP.

The rhesus PGP binding agent may also be an antibody or a functionally active antigen binding antibody fragment.

Antibodies are well known to those of ordinary skill in the science of immunology. As used herein, the term "antibody" means not only intact antibody molecules but also fragments of antibody molecules retaining rhesus PGP binding ability. Such fragments are also well known in the art and are regularly employed both in vitro and in vivo. In particular, as used herein, the term "antibody" means not only intact immunoglobulin molecules but also the well-known active fragments F(ab')$_2$, and Fab. F(ab')$_2$, and Fab fragments which lack the Fc fragment of intact antibody, clear more rapidly from the circulation, and may have less non-specific tissue binding of an intact antibody (Wahl et al., *J. Nucl. Med.* 24:316–325 (1983).

Monoclonal antibodies may be made by any of the methods known in the art utilizing rhesus PGP, or a fragment thereof, as an immunogen. Alternatively the antibody may be a polyclonal antibody specific for rhesus PGP which inhibits rhesus PGP activity. The preparation and use of polyclonal antibodies is also known to one of ordinary skill in the art.

Significantly, as is well known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to antigen epitopes.

The sequences of the antigen-binding Fab' portion of the anti-rhesus PGP monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit rhesus PGP activity are identified. These non-human animal antibodies can be humanized for use in the treatment of a human subject in the methods according to the invention. Examples of methods for humanizing a murine antibody are provided in U.S. Pat. Nos. 4,816,567, 5,225,539, 5,585,089, 5,693,762 and 5,859,205. Other antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-rhesus PGP monoclonal antibody; chimeric antibodies in which the Fc and/or FR and/or CDR1 and/or CDR2 and/or light chain CDR3 regions of an anti-rhesus PGP antibody have been replaced by homologous human or non-human sequences; chimeric F(ab')$_2$ fragment antibodies in which the FR and/or CDR1 and/or CDR2 and/or light chain CDR3 regions of an anti-rhesus PGP antibody have been replaced by homologous human or non-human sequences; and chimeric Fab fragment antibodies in which the FR and/or CDR1 and/or CDR2 and/or light chain CDR3 regions have been replaced by homologous human or non-human sequences.

The rhesus PGP binding agents include molecules of numerous size and type that bind selectively or preferentially to rhesus PGP polypeptides, and complexes of both rhesus PGP polypeptides and their binding partners. These molecules may be derived from a variety of sources. For example, rhesus PGP binding agents can be provided by screening degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the rhesus PGP polypeptide. This process can be repeated through several cycles of reselection of phage that bind to the rhesus PGP polypeptide. Repeated rounds lead to enrichment of phage bearing particular sequences. DNA sequence analysis can be conducted to identify the sequences of the expressed polypeptides. The minimal linear portion of the sequence that binds to the rhesus PGP polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the rhesus PGP polypeptides. Thus, the rhesus PGP polypeptides of the invention, or a fragment thereof, can be used to screen peptide libraries, including phage display libraries, to identify and select peptide binding partners of the rhesus PGP polypeptides of the invention. Such molecules can be used, as described, for screening assays, for purification protocols, for interfering directly with the functioning of rhesus PGP and for other purposes that will be apparent to those of ordinary skill in the art.

Therefore the invention generally provides efficient methods of identifying pharmacological agents or lead compounds for agents useful in the treatment of conditions associated with aberrant PGP activity and the compounds and agents so identified. Generally, the screening methods involve assaying for compounds which inhibit or enhance transport of molecules through rhesus PGP. Such methods are adaptable to automated, high throughput screening of compounds. Examples of such methods are described in U.S. Pat. No. 5,429,921.

A variety of assays for pharmacological agents are provided, including, labeled in vitro protein binding assays, efflux assays using detectable molecules, etc. For example, protein binding screens are used to rapidly examine the binding of candidate pharmacological agents to a rhesus PGP. The candidate pharmacological agents can be derived from, for example, combinatorial peptide libraries. Convenient reagents for such assays are known in the art. An exemplary cell-based assay of efflux involves contacting a cell having a rhesus PGP with a candidate pharmacological agent under conditions whereby the efflux of a detectably labeled molecule can occur. Specific conditions are well known in the art and are described, for example, in Sharom et al., Biochem. Pharmacol. 58:571–586, 1999, and references cited therein. A reduction in the efflux in the presence of the candidate pharmacological agent indicates that the candidate pharmacological agent reduces the efflux activity of rhesus PGP. An increase in the efflux in the presence of the candidate pharmacological agent indicates that the candidate pharmacological agent increases the efflux activity of rhesus PGP.

Rhesus PGP used in the methods of the invention can be added to an assay mixture as an isolated polypeptide (where binding of a candidate pharmaceutical agent is to be measured) or as a cell or other membrane-encapsulated space which includes a rhesus PGP polypeptide. In the latter assay configuration, the cell or other membrane-encapsulated space can contain the rhesus PGP as a preloaded polypeptide or as a nucleic acid (e.g. a cell transfected with an expression vector containing a rhesus PGP). In the assays described herein, the rhesus PGP polypeptide can be produced recombinantly, or isolated from biological extracts, but preferably is synthesized in vitro. Rhesus PGP polypeptides encompass chimeric proteins comprising a fusion of a rhesus PGP polypeptide with another polypeptide, e.g., a polypeptide capable of providing or enhancing protein-protein binding, or enhancing stability of the rhesus PGP polypeptide under assay conditions. A polypeptide fused to a rhesus PGP polypeptide or fragment thereof may also provide means of readily detecting the fusion protein, e.g., by immunological recognition or by fluorescent labeling.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents.

Therefore, a source of candidate agents are libraries of molecules based on known P-glycoprotein inhibitors, in which the structure of the inhibitor is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on existing P-glycoprotein inhibitors.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate pharmacological agent, the rhesus PGP mediates the efflux of a control amount of a compound such as a drug. For determining the binding of a candidate pharmaceutical agent to a rhesus PGP, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of efflux or the level of specific binding between the rhesus PGP polypeptide and the candidate pharmaceutical agent is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a transmembrane transport assay. The transport of a directly or indirectly detectable product, e.g., a fluorescent molecule such as calcein AM or rhodamine 123, is preferred. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a rhesus PGP polypeptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

According to the invention rhesus PGP inhibitors also include "dominant negative" polypeptides derived from SEQ ID NO:2. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the ligand.

The end result of the expression of a dominant negative rhesus PGP polypeptide of the invention in a cell is a reduction in PGP activity such as molecular transport. One of ordinary skill in the art can assess the potential for a dominant negative variant of a rhesus PGP polypeptide, and using standard mutagenesis techniques to create one or more dominant negative variant polypeptides. For example, given the teachings contained herein of a rhesus PGP polypeptide, one of ordinary skill in the art can modify the sequence of the rhesus PGP polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in rhesus PGP activity and/or for retention of such an activity. Other similar methods for creating and testing dominant negative variants of a rhesus PGP polypeptide will be apparent to one of ordinary skill in the art.

Each of the compositions of the invention is useful for a variety of therapeutic and non-therapeutic purposes. For example, the rhesus PGP nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, many labels useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci.* (USA) 80:4045 (1983); Renz, M. et al., *Nucl. Acids Res.* 12:3435 (1984); and Renz, M., *EMBO J.* 6:817 (1983).

Additionally, complements of the rhesus PGP nucleic acids can be useful as antisense oligonucleotides, e.g., by delivering the antisense oligonucleotide to an animal to induce a rhesus PGP "knockout" phenotype. The administration of antisense RNA probes to block gene expression is discussed in Lichtenstein, C., Nature 333:801–802 (1988).

Alternatively, the rhesus PGP nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of rhesus PGP knockout and transgenic animals as models for the study of disorders involving tranport of molecules across cell membranes. A variety of methods known to one of ordinary skill in the art arc available for the production of transgenic animals associated with this invention.

Inactivation or replacement of the endogenous PGP/MDR1 gene can be achieved by a homologous recombination system using embryonic stem cells. The resultant transgenic non-human mammals having a PGP−/− knockout phenotype may be made transgenic for the rhesus PGP and used as a model for screening compounds as modulators (agonists or antagonists/inhibitors) of the rhesus PGP. In this manner, such therapeutic drugs can be identified.

Additionally, a normal or mutant version of rhesus PGP can be inserted into the germ line to produce transgenic animals which constitutively or inducibly express the normal or mutant form of rhesus PGP. These animals are useful in studies to define the role and function of rhesus PGP in cells.

The compositions of the invention are also useful for therapeutic purposes. Accordingly the invention encompasses a method for inhibiting PGP activity in a mammalian cell. The invention further provides methods for reducing or increasing PGP activity in a cell. In one embodiment, the method involves contacting the mammalian cell with an amount of a rhesus PGP nucleic acid or polypeptide effective to inhibit molecular transport out of the mammalian cell. Such methods are useful in vitro for the purpose of, for example, elucidating the mechanisms involved in drug resistance and reduced drug bioavailability.

The invention also encompasses a method for increasing PGP expression in a cell or subject. The amount of rhesus PGP can be increased in such cell or subject by contacting the cell with, or administering to the subject, a PGP nucleic acid or a PGP polypeptide of the invention to the subject in an amount effective to increase transmembrane transport in the cell or the subject. An increase in PGP activity can be measured by the assays described herein, e.g., assays of transmembrane transport.

The preparations of the invention are administered in effective amounts. An effective amount is that amount of a pharmaceutical preparation that alone, or together with further doses, produces the desired response. Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Generally, doses of active compounds would be from about 0.01 mg/kg per day to 1000 mg/kg per day. It is expected that doses ranging from 50–500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compound, although fewer doses typically will be given when compounds are prepared as slow release or sustained release medications.

When administered, the pharmaceutical preparations of the invention are applied in pharmaceutically-acceptable amounts and in pharmaceutically-acceptably compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The rhesus PGP inhibitors or rhesus PGP nucleic acids and polypeptides useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intrathecal, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the rhesus PGP inhibitor or rhesus PGP nucleic acids and polypeptides, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intrathecal, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art. Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention will be more fully understood by reference to the following examples. These examples, however, are merely intended to illustrate the embodiments of the invention and are not to be construed to limit the scope of the invention.

EXAMPLES

Example 1

Cloning and Assembly of Rhesus Monkey PGP cDNA libraries were prepared using rhesus monkey (*Macaca mulatta*) mRNA according to standard procedures. The libraries were screened for P-glycoprotein clones using a human P-glycoprotein DNA probe. Clones were isolated, purified and sequenced in accordance with standard procedures.

Preparation of Library

A custom Lambda ZAP II cDNA library from rhesus monkey liver was prepared by Stratagene. This template was used to obtain clones T3/88, 70/78K, 16/17, and 79/77.

Anticipating that the rhesus monkey would show substantial homology to the human and cynomologous PGP, initial primers were designed based on human and cynomologous PGP nucleotide sequences. PCR primers were also made based on the Lambda ZAP II vector sequence. Later sequencing primers were designed based on the Rhesus monkey sequence or a combination of the rhesus and cynomologous sequences. All primers used are listed below.

| Primer | Sequence | Source | Nucleotides | SEQ ID NO: |
|---|---|---|---|---|
| | | Primers used for PCR | | |
| ps070 | ctg gac ttc ctc tca tga tgc tgg tgt | Human PGP | 188–214F | 12 |
| ps077 | ttg taa tac gac tca cta tag ggc gaa t | T7 Primer | Based on Stratagene seq. | 13 |
| ps078 | ctt ttc gag atg ggt aac tga agt gaa c | Cyno/Human PGP | 1198–1225R | 14 |
| ps079 | aga agg tgc tgg gaa gat cgc tac tga a | Cyno/Human PGP | 2679–2706F | 15 |
| ps088 | cat atc ttc ctc cag att cat gac ggg cac | Cyno/Human PGP | 188–213R | 16 |
| T3 | aag ctc gaa att aac cct cac taa agg | T3 primer | Based on Stratagene seq | 17 |
| sh016 | cgc tgg ttt cga tga tgg agt | Cyno PGP | 1803–1823F | 18 |
| sh017 | cag tcg ggt ggg ata gtt gaa tac | Cyno PGP | 3130–3153R | 19 |
| sh027 | gcc aat att tct ata ggt gct gct t | Cyno PGP | 892–916F | 20 |
| sh028 | ggt ata ctt tca tcc aga gcc tct t | Cyno PGP | 2063–2087R | 21 |
| | | Primers used for Sequencing | | |
| M13F | gta aaa cga cgg cca g | M13F | Based on Invitrogen seq. | 22 |

-continued

| Primer | Sequence | Source | Nucleotides | SEQ ID NO: |
|---|---|---|---|---|
| M13R | cag gaa aca gct atg ac | M13R | Based on Invitrogen seq. | 23 |
| T3 | aag ctc gaa att aac cct cac taa agg | T3 Primer | Based on Stratagene seq. | 17 |
| T7/ps077 | ttg taa tac gac tca cta tag ggc gaa t | T7 Primer | Based on Stratagene seq. | 13 |
| ps079 | aga agg tgc tgg gaa gat cgc tac tga a | Cyno/Human PGP | 2679–2706F | 24 |
| ps080 | gcc taa agc cga aca cat | Cyno PGP | 3083–3100F | 25 |
| sh010 | tta tgc tct ggc ctt ctg gta tgg | Cyno PGP | 936–959F | 26 |
| sh015 | ttg ttt cgg cat cat cat ttc ttg ta | Cyno PGP | 2226–2251R | 27 |
| sh016 | cgc tgg ttt cga tga tgg agt | Cyno PGP | 1803–1823F | 28 |
| sh018 | gct tta ggc ctt ctg tgc tgt ag | Cyno PGP | 3068–3091R | 29 |
| sh019 | gcc aat tat aca cgc ctt ca | Rhesus PGP | 3464–3481F | 30 |
| sh020 | cgc aat gga gga gca gag | Rhesus PGP | 19–35F | 31 |
| sh021 | tcg aat agc tgt caa tac tt | Rhesus PGP | 1127–1146R | 32 |
| sh030 | cag acc tcc att tat aat ggc aca a | Cyno PGP | 2157–2181R | 33 |
| sh031 | gct cat cgt ttg tct acg gtt cgt a | Cyno PGP | 1765–1789F | 34 |

All PCR reactions were performed using a Perkin Elmer 9700 Thermocycler (Norwalk, Conn.). PCR products were analyzed on an agarose gel, and promising bands were purified by the use of Qiaquick Gel Extraction Kit (Qiagen, Valencia, Calif.) according to the manufacturer's instructions. These bands were ligated into pCR 2.1 and transformed into INVαF using Invitrogen's TA Cloning protocol according to the manufacturer's instructions (Invitrogen, Carlsbad, Calif.). White colonies were picked and analyzed by restriction digest. DNA was prepared from promising clones using the Qiagen QIAamp DNA Mini Kit according to the manufacturer's instructions and sequenced with an ABI 377 sequencer (Applied Biosystems, Foster City, Calif.).

Clone T3/88

Using primers T3 and ps088, a ~500 bp fragment was obtained following 40 cycles of TOUCHDOWN™ PCR (Clontech, Palo Alto, Calif.) (94° C. for 5 m; followed by 5 cycles of 94° C. for 30 s, 72° C. for 120 s; 5 cycles of 94° C. for 30 s, 70° C. for 45 s, 72° C. for 120 s, 30 cycles of 94° C. for 30 s, 68° C. for 45 s, 72° C. for 120 s; ending with 72° C. for 7 m) using Advantage® cDNA polymerase (Clontech, Palo Alto, Calif.). This 500 base pair fragment was sequenced with M13F and M13R primers, and resulted in a total of ~350 base pairs corresponding to cynomologous PGP 1–342 (the start codon for cynomologous PGP being at 1). This sequence represents the 5' end of the cDNA and the start codon.

Clone 70/78K

Using primers ps070 and ps078, a ~1.0 kb fragment was obtained following 38 cycles of PCR (94° C. for 5 m; followed by 38 cycles of 94° C. for 30 s, 65° C. for 45 s, 72°C. for 60 s; ending with 72° C. for 5 m) using Klentaq polymerase (Clontech, Palo Alto, Calif.). This was sequenced using M13F and M13R primers. This amplification resulted in a total of ~1.0 kb of sequence corresponding to Cynomologous PGP 194–1222.

Clone 27/28

Using primers sh027 and sh028, a ~1.2 kb fragment was obtained following 40 cycles of TOUCHDOWN™ PCR (94° C. for 5 m; followed by 5 cycles of 94° C. for 30 s, 72° C. for 120 s, 94° C. for 30 s; 5 cycles of 94° C. for 30 s, 70° C. for 45 s, 72° C. for 120 s; 30 cycles of 94° C. for 30 s, 68° C. for 45 s, 72° C. for 120 s; ending with 72° C. for 7 m) using Advantage® cDNA Polymerase (Clontech, Palo Alto, Calif.). This amplification product was sequenced using M13F and M13R primers, and resulted in a total of ~1 kb of sequence corresponding to cynomologous PGP 1032–2200.

Clone 16/17

Using primers sh016 and sh017, a ~1.4 kb fragment was obtained following 35 cycles of PCR (94° C. for 5 m; followed by 35 cycles of 94° C. for 30 s, 55° C. 4 for 5 s, 72° C. for 60 s; ending with 72° C. for 7 m) using Advantage® cDNA Polymerase (Clontech, Palo Alto, Calif.). This was sequenced using M13F and M13R primers. Further sequencing primers, sh024F and sh024R, were designed based on the sequence obtained. This amplification resulted in a total of ~1.3 kb of sequence corresponding to cynomologous PGP 1813–3153.

Clone 79/77

Using primers ps079 and ps077, a ~1.5 kb fragment was obtained following 38 cycles of PCR (94° C. for 5 m; followed by 94° C. for 30 s, 63° C. for 45 s, 72° C. for 60 s; ending with 60 s; ending with 72° C. for 7 m) using Advantage® cDNA Polymerase (Clontech, Palo Alto, Calif.). This was sequenced using M13F and M13R primers. Sequencing primer sh019 was designed based on the sequence obtained. There was a single base pair mutation at position 2945 that was corrected by site directed mutagenesis (Cambridge Bioscience, Cambridge, UK); the change was made from: gta ttt tAa gct (SEQ ID NO: 35) to: gta ttt tCa gct (SEQ ID NO: 36). Sequence corresponding to cynomologous PGP nucleotides 2682–3852 was obtained, which included the stop codon for the rhesus monkey PGP cDNA.

Assembly of the Complete cDNA

Clone 1+2

Clone T3/88 was digested with PvuII. A 535 bp fragment was isolated on a gel and purified using the Qiaquick Gel Extraction Kit (Qiagen, Valencia, Calif.) according to the manufacturer's instructions. XbaI linkers were then added to clone T3/88 and excess linkers were digested with XbaI/EcoRV. The digest was purified using the Qiaquick PCR purification Kit (Qiagen, Valencia, Calif.) according to the manufacturer's instructions. Clone T3/88 was then digested with SacI, and a 286 bp fragment was isolated on a gel and purified using the Qiaquick Gel Extraction Kit (Qiagen, Valencia, Calif.) according to the manufacturer's instructions.

Clone 70/78K was digested with EcoRI/SacI. A 1000 bp fragment was isolated on a gel and purified using the Qiaquick Gel Extraction Kit (Qiagen, Valencia, Calif.) according to the manufacturer's instructions.

These were ligated into Bluescript KS plasmid, digested with XbaI and EcoRI, and dephosphorylated with calf intestinal phosphatase (CIP) and shrimp alkaline phosphatase (SAP). The resulting plasmid is referred to as Clone 1+2/BS KS+.

Clone 3A+3B

Clone 27/28 was digested with EcoRI/BamHI. A 798 bp fragment was isolated on a gel and purified using the Qiaquick Gel Extraction Kit (Qiagen, Valencia, Calif.) according to the manufacturer's instructions.

Clone 16/17 was digested with BamHI/KpnI. An 804 bp fragment was isolated on a gel and purified using the Qiaquick Gel Extraction Kit (Qiagen, Valencia, Calif.) according to the manufacturer's instructions.

These were ligated into pUC19 digested with EcoRI and KpnI restriction endonucleases.

Complete cDNA

Clone 1+2/BS KS+ was digested with EcoRI and HincII restriction endonucleases. The linear plasmid was purified using the Qiaquick PCR Purification Kit (Qiagen, Valencia, Calif.) according to the manufacturer's instructions.

Clone 3A+3B was digested with EcoRI and KpnI restriction endonucleases. A 1602 bp fragment was isolated on a gel and purified using the Qiaquick Gel Extraction Kit (Qiagen, Valencia, Calif.) according to the manufacturer's instructions.

Clone 79/77 was digested with KpnI and DraI restriction endonucleases. An 1109 bp fragment was isolated on a gel and purified using the Qiaquick Gel Extraction Kit (Qiagen, Valencia, Calif.) according to the manufacturer's instructions.

The three foregoing digested DNA molecules were ligated together, and then transformed into SCS-1 Competent Cells (Stratagene, La Jolla, Calif.) according to the manufacturer's instructions. Promising clones were identified by restriction digest, and the identity of the final clone was confirmed by sequencing. There was a base pair deletion (relative to the PCR fragments) at position 120 that resulted in a reading frame shift. This deletion was corrected by site directed mutagenesis (Cambridge Bioscience, Cambridge, UK) which resulted in the insertion of a T nucleotide at position 120 (from ttc aat gtt cgc tat (SEQ ID NO: 37) to: ttc aat gtt Tcg cta t (SEQ ID NO: 38). Sequence correction was confirmed by sequencing.

The nucleotide sequence of the Rhesus P-glycoprotein is presented as SEQ ID NO: 1. The coding sequence consists of nucleotides 1–3852, producing a polypeptide of 1284 amino acids (SEQ ID NO: 2).

Example 2

Activity of Rhesus P-glycoprotein

Materials and Methods

Rhesus monkey PGP cDNA (SEQ ID NO:1) is introduced into a clonal population of LLC-PK1 cells in a vector that confers resistance to hygromycin B. LLC-PK1 cells are obtained from the American Type Culture Collections and are propagated in Medium 199 supplemented to 7% with fetal bovine serum. LLC-PK1 cells are recloned prior to transfection in order to assure homogeneity of the cell population. Briefly, rhesus monkey PGP cDNA is incorporated into the p222CMV vector. This vector is derived from the p220.2 episomal vector system based on the OriP sequences for Epstein Barr virus and the EBNA-1 gene product (Sugden et al., *Mol. Cell Biol.* 5:410–413, 1985; Yates et al., *Nature* (Lond.) 313: 812–815, 1985). The PGP cDNA is under the control of the cytomegalovirus (CMV) immediate early promoter. The vector confers resistance to hygromycin B. Cells (in 0.4 mL) and DNA (10 to 20 µg) were transfected by electroporation using a BTX Electro cell manipulator model 600 using a 2 mm gap cell, 100V, 2500 µF capacitance and 72 ohm resistance. After electroporation, the cells are plated in multiwell plates (48 well, Corning Costar) at 10% of confluence. One to two days after transfection hygromycin B is introduced at a final concentration of 400 to 600 µg/ml. Cells are refed every 2 to 4 days and are propagated in 400 to 600 µg/ml hygromycin B for 6 to 8 days at which point the bulk of the wild type cells are detached. The hygromycin B is reduced to 100 µg/ml and maintained in this concentration of hygromycin B. After 14 to 18 days the wells are inspected and wells containing single colonies are trypsinized and scaled up to bulk cultures. Expression of PGP is measured by the polarization of vinblastine (0.1 µM) transport in Transwells™.

LLC-PK1 cell based transport studies are conducted in 24 well Transwells™ (Corning Costar, Catalog number 3415). Transwells™ are prepared by the addition of 0.6 mL media to the basolateral space and 0.1 mL media to the apical space. Cells are seeded at $4\times10^4$ cells per insert (typically in 0.05 mL to 0.15 mL), refed with fresh media every 2 to 4 days and used for transport studies 4 to 8 days post seeding. Transport assays are conducted in Hank's balanced saline (HBSS) buffered with 10 mM HEPES (pH 7 to 7.2). Cell monolayers are rinsed with HBSS prior to use in transport assays. Transport is measured under sink conditions in both the apical to basolateral (A to B) and basolateral to apical (B to A) directions. At least duplicate monolayers are used per determination. At the desired time points, samples are withdrawn from the receiver chamber (apical or basolateral chambers). Quantitation of the amount of compound transported is by liquid scintillation counting (vinblastine) or HPLC with UV or mass spectrometric detection.

Rhesus PGP cDNA is expressed in insect cells using a baculovirus vector. Membranes are prepared according to the method of (Sarkadi et al., *J Biol. Chem.* 267: 4854–4858, 1992) and stored at −80° C. until use. ATPase assays are conducted in 96 well microtiter plates. The assays are conducted using a modification of the methods of (Sarkadi et al., 1992 and Druekes et al., *Anal. Biochem.* 230: 173–177, 1995).

A detailed method for each well of a 96 well plate is contained below: A 0.06 ml reaction mixture containing 40 µg membranes, 20 µM Verapamil (positive control) or test drug, and 3–5 mM MgATP, in buffer containing 50 mM Tris-MES, 2 mM EGTA, 50 mM KCl, 2 mM dithiothreitol, and 5 mM sodium azide, is incubated at 37° C. for 20 min. An identical reaction mixture containing 100 µM sodium orthovanadate is assayed in parallel. Orthovanadate inhibits PGP by trapping MgADP in the nucleotide binding site. Thus, ATPase activity measured in the presence of orthovanadate represents non-PGP ATPase activity and can be subtracted from the activity generated without orthovanadate to yield vanadate-sensitive ATPase activity. The reaction is stopped by the addition of 30 µl of 10% SDS+ Antifoam A. Two additional reaction mixtures (+ and − orthovanadate) but without MgATP, are also prepared and incubated with the others, and then supplemented with SDS and MgATP, to represent time=0 min of reaction. The incubations are followed with addition of 200 µl of 35 mM ammonium molybdate in 15 mM zinc acetate:10% ascorbic acid (1:4) and incubated for an additional 20 min at 37° C. The liberation of inorganic phosphate is detected by its absorbance at 800 nm and quantitated by comparing the absorbance to a phosphate standard curve.

Ligand binding assays and assays for measuring inhibition of fluorescent dye uptake are preformed as described by Sharom et al. (*Biochem. Pharmacol.* 58:571–586, 1999).

I. Stable PGP Expression in LLC-PK1 Cells.

Functional expression of rhesus monkey PGP is measured by the polarization of transport of vinblastine. Control cells typically demonstrate a B to A/A to B ratio of between 1 and 3. PGP transfected cells demonstrate a much higher ratio. The expression of cDNA-derived rhesus monkey is stable.

II. Activation of ATPase Activity in PGP Membranes.

The stimulation of ATPase assay provides a rapid measure of the concentration dependence of any interaction of a drug with PGP. The liberated inorganic phosphate is measured by a simple spectrophotometric assay performed in a microtiter plate format. The testing of multiple drug concentrations allows estimation of the affinity of the drug for PGP and whether saturation of the response was observed.

III. Drug Transport Across Cell Monolayers.

The ATPase assay does not directly measure drug transport. In order to examine the concordance between activation of ATPase and actual transport, the rates of transport of the drugs are measured in control LLC-PK1 and rhesus monkey PGP cell monolayers. For each drug concentration, four measurements are made:

| A: | A to B | Control cells |
|----|--------|---------------|
| B: | B to A | Control cells |
| C: | A to B | PGP cells |
| D: | B to A | PGP cells |

The polarization of transport is calculated in control cells (B/A) and PGP cells (D/C). The intrinsic activity (IA) of PGP is calculated as the sum of the amount PGP facilitated B to A transport in PGP cells relative to control cells (D minus B) and the amount that PGP impeded A to B transport in PGP cells relative to control cells (A minus C). The intrinsic clearance of PGP is calculated from a plot of the concentration dependence data by either calculating the slope of the line under non-saturating conditions or from the calculated apparent Km and Vmax values when saturation is observed. Intrinsic clearance is expressed as $mL/m^2/min$.

The ATPase data provides useful concentration response data. For example, the apparent Km values for some compounds are in good agreement between the ATPase and transport systems. However, other drugs activate ATPase activity but transport by PGP is not detectable. At the least, ATPase assay can identify a concentration range below which the response to transport by PGP was linear with respect to drug concentration. This should allow simplification of the experimental design for measuring the intrinsic clearance of PGP, an important consideration if large numbers of compounds are to be tested.

IV. Bioavailability

Bioavailability studies are performed by performing one or more of the assays described above with two or more different PGP types. The different PGP types can be different species (e.g., dog and human, rhesus monkey and human, dog and rhesus monkey, etc.) or can be different alleles of the same species. The results of these assays are compared to determine or estimate the bioavailability of a drug in individuals of the different species or in individuals that express different PGP alleles. The results of one determination also may be compared to a previously determined value of, e.g., ATPase or transport, as an historical control.

Each of the foregoing patents, patent applications and references is hereby incorporated by reference.

While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. An isolated nucleic acid molecule that encodes the amino acid sequence of SEQ ID NO:2 and complements thereof.

2. An isolated nucleic acid molecule that encodes the amino acid seuuence of SEQ ID NO:2, wherein the isolated nucleic acid molecule comprises the nucleotide sequence of SEQ ID NO: 1.

3. An expression vector comprising the isolated nucleic acid molecule of claim 1 operably linked to a promoter.

4. An expression vector comprising the isolated nucleic acid molecule of claim 2 operably linked to a promoter.

5. A host cell transformed or transfected with the expression vector of claim 3.

6. A host cell transformed or transfected with the expression vector of claim 4.

* * * * *

UNITED STATES PATENT AND TRADEMARK OFFICE
CERTIFICATE OF CORRECTION

PATENT NO. : 6,855,812 B2
DATED : February 15, 2005
INVENTOR(S) : Hanscom et al.

It is certified that error appears in the above-identified patent and that said Letters Patent is hereby corrected as shown below:

Title page,
Item [56], References Cited, FOREIGN PATENT DOCUMENTS, change "WO 199961589 A2" to -- WO 199964589 A2 --.

Column 111,
Line 54, change "SEO" to -- SEQ --.
Line 56, change "SEO" to -- SEQ --; and change "seuuence" to -- sequence --.

Signed and Sealed this

Thirty-first Day of May, 2005

JON W. DUDAS
*Director of the United States Patent and Trademark Office*

SEQUENCE LISTING

<160> NUMBER OF SEQ ID NOS: 38

<210> SEQ ID NO 1
<211> LENGTH: 3852
<212> TYPE: DNA
<213> ORGANISM: Macaca mulatta
<220> FEATURE:
<221> NAME/KEY: CDS
<222> LOCATION: (1)..(3852)

<400> SEQUENCE: 1

```
atg gat ctt gaa ggg gac cgc aat gga gga gca gag aag aag aac ttt      48
Met Asp Leu Glu Gly Asp Arg Asn Gly Gly Ala Glu Lys Lys Asn Phe
1               5                   10                  15 ttt aaa ctg aac aat aaa agt aaa aaa gat aag aag gaa agg aaa cca      96
Phe Lys Leu Asn Asn Lys Ser Lys Lys Asp Lys Lys Glu Arg Lys Pro
            20                  25                  30 act gtc agt gta ttt tca atg ttt cgc tat tca aat tgg ctt gac aag     144
Thr Val Ser Val Phe Ser Met Phe Arg Tyr Ser Asn Trp Leu Asp Lys
        35                  40                  45 ttg tat atg gtg gtg gga att ttg gct gcc atc atc cat gga gct gga     192
Leu Tyr Met Val Val Gly Ile Leu Ala Ala Ile Ile His Gly Ala Gly
    50                  55                  60 ctt cct ctc atg atg ctg gtg ttt gga gac atg acg gat acc ttt gca     240
Leu Pro Leu Met Met Leu Val Phe Gly Asp Met Thr Asp Thr Phe Ala
```

-continued

```
                  65                    70                    75                    80
aat gca gga aat tta gga gat tta gga gct ctg ttg ttt aac aac act          288
Asn Ala Gly Asn Leu Gly Asp Leu Gly Ala Leu Leu Phe Asn Asn Thr
                     85                    90                    95 aat agc agt aat atc act gat aca gtg ccc gtc atg aat ctg gag gaa          336
Asn Ser Ser Asn Ile Thr Asp Thr Val Pro Val Met Asn Leu Glu Glu
                100                   105                   110 gat atg acc agg tat gcc tat tat tac agt gga att ggt gct ggg gtg          384
Asp Met Thr Arg Tyr Ala Tyr Tyr Tyr Ser Gly Ile Gly Ala Gly Val
                115                   120                   125 ctg gtt gct gct tac att cag gtt tca ttt tgg tgc ctg gca gct gga          432
Leu Val Ala Ala Tyr Ile Gln Val Ser Phe Trp Cys Leu Ala Ala Gly
            130                   135                   140 aga caa ata cac aaa att aga aaa cag ttt ttt cat gct ata atg cga          480
Arg Gln Ile His Lys Ile Arg Lys Gln Phe Phe His Ala Ile Met Arg
145                   150                   155                   160 cag gag ata ggc tgg ttt gat gtg cac gat gtt ggg gag ctt aac acc          528
Gln Glu Ile Gly Trp Phe Asp Val His Asp Val Gly Glu Leu Asn Thr
                165                   170                   175 cgg ctt aca gat gat gtc tcc aag att aat gaa gga att ggt gac aaa          576
Arg Leu Thr Asp Asp Val Ser Lys Ile Asn Glu Gly Ile Gly Asp Lys
                180                   185                   190 att gga atg ttc ttt cag tca atg gca aca ttt ttc act ggg ttt ata          624
Ile Gly Met Phe Phe Gln Ser Met Ala Thr Phe Phe Thr Gly Phe Ile
                195                   200                   205 gta gga ttt aca cgt ggt tgg aag cta acc ctt gtg att tgg gcc atc          672
Val Gly Phe Thr Arg Gly Trp Lys Leu Thr Leu Val Ile Leu Ala Ile
            210                   215                   220 agt cct gtt ctt gga gtg tca gct gca gcc tgg gca aag ata ctg tct          720
Ser Pro Val Leu Gly Val Ser Ala Ala Ala Trp Ala Lys Ile Leu Ser
225                   230                   235                   240 tca ttt act gat aaa gaa ctc tta gct tat gca aaa gct gga gca gta          768
Ser Phe Thr Asp Lys Glu Leu Leu Ala Tyr Ala Lys Ala Gly Ala Val
                245                   250                   255 gct gaa gag gtc ttg gca gca att aga act gtg att gca ttt gga gga          816
Ala Glu Glu Val Leu Ala Ala Ile Arg Thr Val Ile Ala Phe Gly Gly
                260                   265                   270 caa aag aaa gaa ctc gaa agg tac aac aaa aat tta gaa gaa gct aaa          864
Gln Lys Lys Glu Leu Glu Arg Tyr Asn Lys Asn Leu Glu Glu Ala Lys
            275                   280                   285 aga att ggg ata aag aaa gct att aca gcc aat att tct ata ggt gct          912
Arg Ile Gly Ile Lys Lys Ala Ile Thr Ala Asn Ile Ser Ile Gly Ala
            290                   295                   300 gct ttc ctg ctt atc tat gca tct tat gct ctg gcc ttc tgg tat ggg          960
Ala Phe Leu Leu Ile Tyr Ala Ser Tyr Ala Leu Ala Phe Trp Tyr Gly
305                   310                   315                   320 acc acc ttg gtc ctc tca aag gaa tat tct att gga caa gta ctc act         1008
Thr Thr Leu Val Leu Ser Lys Glu Tyr Ser Ile Gly Gln Val Leu Thr
                325                   330                   335 gta ttc ttt tct gta tta att ggg gct ttt agt gtt gga cag gca tct         1056
Val Phe Phe Ser Val Leu Ile Gly Ala Phe Ser Val Gly Gln Ala Ser
                340                   345                   350 cca agc att gaa gca ttt gca aat gca aga gga gca gct ttt gaa atc         1104
Pro Ser Ile Glu Ala Phe Ala Asn Ala Arg Gly Ala Ala Phe Glu Ile
            355                   360                   365 ttc aag ata att gat aat aag cca agt att gac agc tat tcg aag agt         1152
Phe Lys Ile Ile Asp Asn Lys Pro Ser Ile Asp Ser Tyr Ser Lys Ser
            370                   375                   380 ggg cac aaa cca gat aat att aag gga aat ttg gaa ttc aga aat gtt         1200
```

```
              Gly His Lys Pro Asp Asn Ile Lys Gly Asn Leu Glu Phe Arg Asn Val
              385                 390                 395                 400 cac ttc agt tac cca tct cga aaa gaa gtt aag atc ttg aag ggc ctg           1248
His Phe Ser Tyr Pro Ser Arg Lys Glu Val Lys Ile Leu Lys Gly Leu
                    405                 410                 415 aac ctg aag gtg cag agt ggg cag acg gtg gcc ctg gtt gga aac agc           1296
Asn Leu Lys Val Gln Ser Gly Gln Thr Val Ala Leu Val Gly Asn Ser
                420                 425                 430 ggc tgt ggg aag agc aca acg gtc cag ctg atg cag agg ctt tat gac           1344
Gly Cys Gly Lys Ser Thr Thr Val Gln Leu Met Gln Arg Leu Tyr Asp
            435                 440                 445 ccc aca gag ggc atg gtc agt gtt gat gga cag gat att agg acc ata           1392
Pro Thr Glu Gly Met Val Ser Val Asp Gly Gln Asp Ile Arg Thr Ile
        450                 455                 460 aac gta agg ttt cta cgg gaa atc atc ggt gtg gtg agt cag gaa cct           1440
Asn Val Arg Phe Leu Arg Glu Ile Ile Gly Val Val Ser Gln Glu Pro
465                 470                 475                 480 gta ttg ttt gcc acc acg ata gct gaa aac att cgc tat ggt cgt gaa           1488
Val Leu Phe Ala Thr Thr Ile Ala Glu Asn Ile Arg Tyr Gly Arg Glu
                    485                 490                 495 gat gtc acc atg gat gag att gag aaa gct gtc aag gaa gcc aat gcc           1536
Asp Val Thr Met Asp Glu Ile Glu Lys Ala Val Lys Glu Ala Asn Ala
                500                 505                 510 tat gac ttt atc atg aaa ctg cct cag aaa ttt gac acc ctg gtt gga           1584
Tyr Asp Phe Ile Met Lys Leu Pro Gln Lys Phe Asp Thr Leu Val Gly
            515                 520                 525 gag aga ggg gcc cag ctg agt ggt ggg cag aag cag agg atc gcc att           1632
Glu Arg Gly Ala Gln Leu Ser Gly Gly Gln Lys Gln Arg Ile Ala Ile
        530                 535                 540 gca cgt gcc ctg gtt cgc aac ccc aag atc ctc ctg ctg gac gag gcc           1680
Ala Arg Ala Leu Val Arg Asn Pro Lys Ile Leu Leu Leu Asp Glu Ala
545                 550                 555                 560 acg tca gcc ttg gac aca gaa agt gaa gca gtg gtt cag gtg gct ctg           1728
Thr Ser Ala Leu Asp Thr Glu Ser Glu Ala Val Val Gln Val Ala Leu
                    565                 570                 575 gat aag gcc aga aaa ggt cgg acc acc att gtg ata gct cat cgt ttg           1776
Asp Lys Ala Arg Lys Gly Arg Thr Thr Ile Val Ile Ala His Arg Leu
                580                 585                 590 tct acg gtt cgt aat gcc gac gtc atc gct ggt ttc gat gat gga gtc           1824
Ser Thr Val Arg Asn Ala Asp Val Ile Ala Gly Phe Asp Asp Gly Val
            595                 600                 605 att gtg gag aaa gga aat cat gat gag ctc atg aaa gag aaa ggc att           1872
Ile Val Glu Lys Gly Asn His Asp Glu Leu Met Lys Glu Lys Gly Ile
        610                 615                 620 tac ttc aaa ctt gtc aca atg cag aca gca gga aat gaa att gaa tta           1920
Tyr Phe Lys Leu Val Thr Met Gln Thr Ala Gly Asn Glu Ile Glu Leu
625                 630                 635                 640 gaa aat gca gct gat gaa tcc aaa agt gaa att gat acc ttg gaa atg           1968
Glu Asn Ala Ala Asp Glu Ser Lys Ser Glu Ile Asp Thr Leu Glu Met
                    645                 650                 655 tct tca cat gat tca gga tcc agt cta ata aga aaa aga tcc act cgt           2016
Ser Ser His Asp Ser Gly Ser Ser Leu Ile Arg Lys Arg Ser Thr Arg
                660                 665                 670 agg agt gtc cgt gga tca caa ggc caa gac aga aag ctt agt acc aaa           2064
Arg Ser Val Arg Gly Ser Gln Gly Gln Asp Arg Lys Leu Ser Thr Lys
            675                 680                 685 gag gct ctg gat gaa agt ata cct cca gtt tcc ttt tgg agg att atg           2112
Glu Ala Leu Asp Glu Ser Ile Pro Pro Val Ser Phe Trp Arg Ile Met
    690                 695                 700
```

-continued

| | |
|---|---|
| aag cta aat tta act gag tgg cct tat ttt gtt gtt ggt gta ttt tgt<br>Lys Leu Asn Leu Thr Glu Trp Pro Tyr Phe Val Val Gly Val Phe Cys<br>705                       710                       715                      720 | 2160 |
| gcc att ata aat gga ggt ctg caa cca gca ttt gca gta ata ttt tca<br>Ala Ile Ile Asn Gly Gly Leu Gln Pro Ala Phe Ala Val Ile Phe Ser<br>                  725                       730                       735 | 2208 |
| aag att ata ggg att ttt aca aga aat gat gat gcc gaa aca aaa cga<br>Lys Ile Ile Gly Ile Phe Thr Arg Asn Asp Asp Ala Glu Thr Lys Arg<br>                740                       745                      750 | 2256 |
| cag aat agt aac ttg ttt tca cta ttg ttt cta gtc ctt gga att gtt<br>Gln Asn Ser Asn Leu Phe Ser Leu Leu Phe Leu Val Leu Gly Ile Val<br>              755                       760                   765 | 2304 |
| tct ttt att aca ttt ttc ctt cag ggc ttc aca ttt ggc aaa gct gga<br>Ser Phe Ile Thr Phe Phe Leu Gln Gly Phe Thr Phe Gly Lys Ala Gly<br>770                       775                       780 | 2352 |
| gag atc ctc acc aag cgg ctc cga tac atg gtt ttc cga tcc atg ctc<br>Glu Ile Leu Thr Lys Arg Leu Arg Tyr Met Val Phe Arg Ser Met Leu<br>785                       790                       795                   800 | 2400 |
| aga cag gat gtg agc tgg ttt gat gac cct aaa aac acc act gga gca<br>Arg Gln Asp Val Ser Trp Phe Asp Asp Pro Lys Asn Thr Thr Gly Ala<br>                  805                       810                      815 | 2448 |
| ttg act acc agg ctc gcc aat gat gct gct caa gtt aaa ggg gct ata<br>Leu Thr Thr Arg Leu Ala Asn Asp Ala Ala Gln Val Lys Gly Ala Ile<br>820                       825                       830 | 2496 |
| ggt tcc agg ctt gct ata att acc cag aat ata gca aat ctt ggg aca<br>Gly Ser Arg Leu Ala Ile Ile Thr Gln Asn Ile Ala Asn Leu Gly Thr<br>               835                       840                     845 | 2544 |
| gga ata att ata tcc tta atc tat ggt tgg caa ctg aca ctg tta ctc<br>Gly Ile Ile Ile Ser Leu Ile Tyr Gly Trp Gln Leu Thr Leu Leu Leu<br>850                       855                       860 | 2592 |
| tta gca att gta ccc atc att gca ata gca gga gtt gtt gaa atg aaa<br>Leu Ala Ile Val Pro Ile Ile Ala Ile Ala Gly Val Val Glu Met Lys<br>865                       870                       875                   880 | 2640 |
| atg ttg tct gga caa gca ctg aaa gat aag aaa gaa cta gaa ggt gct<br>Met Leu Ser Gly Gln Ala Leu Lys Asp Lys Lys Glu Leu Glu Gly Ala<br>                  885                       890                      895 | 2688 |
| ggg aag atc gct act gaa gca ata gaa aac ttc cga act gtt gtt tct<br>Gly Lys Ile Ala Thr Glu Ala Ile Glu Asn Phe Arg Thr Val Val Ser<br>               900                       905                     910 | 2736 |
| ttg act cag gag cag aag ttt gaa cat atg tat gat cag agt ttg cag<br>Leu Thr Gln Glu Gln Lys Phe Glu His Met Tyr Asp Gln Ser Leu Gln<br>             915                       920                     925 | 2784 |
| gta cca tac aga aac tct ttg agg aaa gca cac atc ttt gga atc acg<br>Val Pro Tyr Arg Asn Ser Leu Arg Lys Ala His Ile Phe Gly Ile Thr<br>930                       935                       940 | 2832 |
| ttt tcc ttc acc cag gca atg atg tat ttt tcc tat gct gga tgt ttc<br>Phe Ser Phe Thr Gln Ala Met Met Tyr Phe Ser Tyr Ala Gly Cys Phe<br>945                       950                       955                   960 | 2880 |
| cgg ttt gga gcc tac ttg gtg gca cat agt ctc atg agc ttt gag gat<br>Arg Phe Gly Ala Tyr Leu Val Ala His Ser Leu Met Ser Phe Glu Asp<br>               965                       970                     975 | 2928 |
| gtt ctg tta gta ttt tca gct gtt gtc ttt ggt gcc atg gcc gtg ggg<br>Val Leu Leu Val Phe Ser Ala Val Val Phe Gly Ala Met Ala Val Gly<br>980                       985                       990 | 2976 |
| caa gtc agt tca ttt gct cct gac tat gcc aaa gcc aaa gta tca gca<br>Gln Val Ser Ser Phe Ala Pro Asp Tyr Ala Lys Ala Lys Val Ser Ala<br>             995                     1000                    1005 | 3024 |
| gcc cac atc atc atg atc att gaa aaa acc cct ttg att gac agc<br>Ala His Ile Ile Met Ile Ile Glu Lys Thr Pro Leu Ile Asp Ser<br>1010                     1015                    1020 | 3069 |

-continued

| | | |
|---|---|---|
| tac agc aca gaa ggc cta aag ccg aac aca ttg gaa gga aat gtc<br>Tyr Ser Thr Glu Gly Leu Lys Pro Asn Thr Leu Glu Gly Asn Val<br>1025                       1030                    1035 | 3114 | |
| aca ttt aat gaa gtt gta ttc aac tat ccc acc cga ctg gac atc<br>Thr Phe Asn Glu Val Val Phe Asn Tyr Pro Thr Arg Leu Asp Ile<br>1040                       1045                    1050 | 3159 | |
| cca gtg ctt cag ggg ctg agc ctg gaa gtg aag aag ggc cag aca<br>Pro Val Leu Gln Gly Leu Ser Leu Glu Val Lys Lys Gly Gln Thr<br>1055                       1060                    1065 | 3204 | |
| ctg gcc ctg gtg ggc agc agt ggc tgt ggg aag agc acg gtg gtc<br>Leu Ala Leu Val Gly Ser Ser Gly Cys Gly Lys Ser Thr Val Val<br>1070                       1075                    1080 | 3249 | |
| cag ctc ctg gag cgg ttc tat gac ccc ttg gcg ggg aaa gtg ctg<br>Gln Leu Leu Glu Arg Phe Tyr Asp Pro Leu Ala Gly Lys Val Leu<br>1085                       1090                    1095 | 3294 | |
| ctt gac ggc aaa gaa ata aag caa ctg aat gtt cag tgg ctc cga<br>Leu Asp Gly Lys Glu Ile Lys Gln Leu Asn Val Gln Trp Leu Arg<br>1100                       1105                    1110 | 3339 | |
| gca cac ctg ggc atc gtg tcc cag gag ccc atc ctg ttt gac tgc<br>Ala His Leu Gly Ile Val Ser Gln Glu Pro Ile Leu Phe Asp Cys<br>1115                       1120                    1125 | 3384 | |
| agc att agt gag aac att gcc tat gga gac aac agc cgg gtg gtg<br>Ser Ile Ser Glu Asn Ile Ala Tyr Gly Asp Asn Ser Arg Val Val<br>1130                       1135                    1140 | 3429 | |
| tca cag gaa gag atc gtg agg gca gcc aag gag gcc aat ata cac<br>Ser Gln Glu Glu Ile Val Arg Ala Ala Lys Glu Ala Asn Ile His<br>1145                       1150                    1155 | 3474 | |
| gcc ttc atc gag tca ctg cct aat aaa tat agc acc aga gta gga<br>Ala Phe Ile Glu Ser Leu Pro Asn Lys Tyr Ser Thr Arg Val Gly<br>1160                       1165                    1170 | 3519 | |
| gac aaa gga act cag ctc tct ggt ggc cag aaa caa cgc att gcc<br>Asp Lys Gly Thr Gln Leu Ser Gly Gly Gln Lys Gln Arg Ile Ala<br>1175                       1180                    1185 | 3564 | |
| ata gct cgt gcc ctt gtt aga cag cct cat att ttg ctt ttg gat<br>Ile Ala Arg Ala Leu Val Arg Gln Pro His Ile Leu Leu Leu Asp<br>1190                       1195                    1200 | 3609 | |
| gaa gcc aca tca gct ctg gat aca gaa agt gaa aag gtt gtc caa<br>Glu Ala Thr Ser Ala Leu Asp Thr Glu Ser Glu Lys Val Val Gln<br>1205                       1210                    1215 | 3654 | |
| gaa gcc ctg gac aaa gcc aga gaa ggc cgt acc tgc att gtg att<br>Glu Ala Leu Asp Lys Ala Arg Glu Gly Arg Thr Cys Ile Val Ile<br>1220                       1225                    1230 | 3699 | |
| gct cac cgc ctg tcc acc atc cag aat gca gac tta ata gtg gtg<br>Ala His Arg Leu Ser Thr Ile Gln Asn Ala Asp Leu Ile Val Val<br>1235                       1240                    1245 | 3744 | |
| ttt cag aat ggc aga gtc aag gag cac ggc aca cat cag cag ctg<br>Phe Gln Asn Gly Arg Val Lys Glu His Gly Thr His Gln Gln Leu<br>1250                       1255                    1260 | 3789 | |
| ctg gca cag aaa ggc atc tat ttt tca atg gtc agt gtc cag gct<br>Leu Ala Gln Lys Gly Ile Tyr Phe Ser Met Val Ser Val Gln Ala<br>1265                       1270                    1275 | 3834 | |
| gga gca aag cgc cag tga<br>Gly Ala Lys Arg Gln<br>1280 | 3852 | |

<210> SEQ ID NO 2
<211> LENGTH: 1283
<212> TYPE: PRT
<213> ORGANISM: Macaca mulatta

<400> SEQUENCE: 2

```
Met Asp Leu Glu Gly Asp Arg Asn Gly Gly Ala Glu Lys Lys Asn Phe
  1               5                  10                  15
Phe Lys Leu Asn Asn Lys Ser Lys Lys Asp Lys Lys Glu Arg Lys Pro
             20                  25                  30
Thr Val Ser Val Phe Ser Met Phe Arg Tyr Ser Asn Trp Leu Asp Lys
         35                  40                  45
Leu Tyr Met Val Val Gly Ile Leu Ala Ala Ile Ile His Gly Ala Gly
     50                  55                  60
Leu Pro Leu Met Met Leu Val Phe Gly Asp Met Thr Asp Thr Phe Ala
 65                  70                  75                  80
Asn Ala Gly Asn Leu Gly Asp Leu Gly Ala Leu Leu Phe Asn Asn Thr
                 85                  90                  95
Asn Ser Ser Asn Ile Thr Asp Thr Val Pro Val Met Asn Leu Glu Glu
            100                 105                 110
Asp Met Thr Arg Tyr Ala Tyr Tyr Ser Gly Ile Gly Ala Gly Val
        115                 120                 125
Leu Val Ala Ala Tyr Ile Gln Val Ser Phe Trp Cys Leu Ala Ala Gly
130                 135                 140
Arg Gln Ile His Lys Ile Arg Lys Gln Phe His Ala Ile Met Arg
145                 150                 155                 160
Gln Glu Ile Gly Trp Phe Asp Val His Asp Val Gly Glu Leu Asn Thr
                165                 170                 175
Arg Leu Thr Asp Asp Val Ser Lys Ile Asn Glu Gly Ile Gly Asp Lys
            180                 185                 190
Ile Gly Met Phe Phe Gln Ser Met Ala Thr Phe Phe Thr Gly Phe Ile
        195                 200                 205
Val Gly Phe Thr Arg Gly Trp Lys Leu Thr Leu Val Ile Leu Ala Ile
210                 215                 220
Ser Pro Val Leu Gly Val Ser Ala Ala Ala Trp Ala Lys Ile Leu Ser
225                 230                 235                 240
Ser Phe Thr Asp Lys Glu Leu Leu Ala Tyr Ala Lys Ala Gly Ala Val
                245                 250                 255
Ala Glu Glu Val Leu Ala Ala Ile Arg Thr Val Ile Ala Phe Gly Gly
            260                 265                 270
Gln Lys Lys Glu Leu Glu Arg Tyr Asn Lys Asn Leu Glu Glu Ala Lys
        275                 280                 285
Arg Ile Gly Ile Lys Lys Ala Ile Thr Ala Asn Ile Ser Ile Gly Ala
290                 295                 300
Ala Phe Leu Leu Ile Tyr Ala Ser Tyr Ala Leu Ala Phe Trp Tyr Gly
305                 310                 315                 320
Thr Thr Leu Val Leu Ser Lys Glu Tyr Ser Ile Gly Gln Val Leu Thr
                325                 330                 335
Val Phe Phe Ser Val Leu Ile Gly Ala Phe Ser Val Gly Gln Ala Ser
            340                 345                 350
Pro Ser Ile Glu Ala Phe Ala Asn Ala Arg Gly Ala Ala Phe Glu Ile
        355                 360                 365
Phe Lys Ile Ile Asp Asn Lys Pro Ser Ile Asp Ser Tyr Ser Lys Ser
370                 375                 380
Gly His Lys Pro Asp Asn Ile Lys Gly Asn Leu Glu Phe Arg Asn Val
385                 390                 395                 400
His Phe Ser Tyr Pro Ser Arg Lys Glu Val Lys Ile Leu Lys Gly Leu
                405                 410                 415
```

-continued

```
Asn Leu Lys Val Gln Ser Gly Gln Thr Val Ala Leu Val Gly Asn Ser
        420                 425                 430
Gly Cys Gly Lys Ser Thr Thr Val Gln Leu Met Gln Arg Leu Tyr Asp
        435                 440                 445
Pro Thr Glu Gly Met Val Ser Val Asp Gly Gln Asp Ile Arg Thr Ile
        450                 455                 460
Asn Val Arg Phe Leu Arg Glu Ile Ile Gly Val Val Ser Gln Glu Pro
465                 470                 475                 480
Val Leu Phe Ala Thr Thr Ile Ala Glu Asn Ile Arg Tyr Gly Arg Glu
                485                 490                 495
Asp Val Thr Met Asp Glu Ile Glu Lys Ala Val Lys Glu Ala Asn Ala
        500                 505                 510
Tyr Asp Phe Ile Met Lys Leu Pro Gln Lys Phe Asp Thr Leu Val Gly
        515                 520                 525
Glu Arg Gly Ala Gln Leu Ser Gly Gly Gln Lys Gln Arg Ile Ala Ile
        530                 535                 540
Ala Arg Ala Leu Val Arg Asn Pro Lys Ile Leu Leu Leu Asp Glu Ala
545                 550                 555                 560
Thr Ser Ala Leu Asp Thr Glu Ser Glu Ala Val Val Gln Val Ala Leu
                565                 570                 575
Asp Lys Ala Arg Lys Gly Arg Thr Thr Ile Val Ile Ala His Arg Leu
        580                 585                 590
Ser Thr Val Arg Asn Ala Asp Val Ile Ala Gly Phe Asp Asp Gly Val
        595                 600                 605
Ile Val Glu Lys Gly Asn His Asp Glu Leu Met Lys Glu Lys Gly Ile
        610                 615                 620
Tyr Phe Lys Leu Val Thr Met Gln Thr Ala Gly Asn Glu Ile Glu Leu
625                 630                 635                 640
Glu Asn Ala Ala Asp Glu Ser Lys Ser Glu Ile Asp Thr Leu Glu Met
                645                 650                 655
Ser Ser His Asp Ser Gly Ser Ser Leu Ile Arg Lys Arg Ser Thr Arg
        660                 665                 670
Arg Ser Val Arg Gly Ser Gln Gly Gln Asp Arg Lys Leu Ser Thr Lys
        675                 680                 685
Glu Ala Leu Asp Glu Ser Ile Pro Pro Val Ser Phe Trp Arg Ile Met
        690                 695                 700
Lys Leu Asn Leu Thr Glu Trp Pro Tyr Phe Val Val Gly Val Phe Cys
705                 710                 715                 720
Ala Ile Ile Asn Gly Gly Leu Gln Pro Ala Phe Ala Val Ile Phe Ser
                725                 730                 735
Lys Ile Ile Gly Ile Phe Thr Arg Asn Asp Asp Ala Glu Thr Lys Arg
        740                 745                 750
Gln Asn Ser Asn Leu Phe Ser Leu Leu Phe Leu Val Leu Gly Ile Val
        755                 760                 765
Ser Phe Ile Thr Phe Phe Leu Gln Gly Phe Thr Phe Gly Lys Ala Gly
        770                 775                 780
Glu Ile Leu Thr Lys Arg Leu Arg Tyr Met Val Phe Arg Ser Met Leu
785                 790                 795                 800
Arg Gln Asp Val Ser Trp Phe Asp Asp Pro Lys Asn Thr Thr Gly Ala
                805                 810                 815
Leu Thr Thr Arg Leu Ala Asn Asp Ala Ala Gln Val Lys Gly Ala Ile
        820                 825                 830
```

-continued

```
Gly Ser Arg Leu Ala Ile Ile Thr Gln Asn Ile Ala Asn Leu Gly Thr
        835                 840                 845
Gly Ile Ile Ile Ser Leu Ile Tyr Gly Trp Gln Leu Thr Leu Leu Leu
    850                 855                 860
Leu Ala Ile Val Pro Ile Ala Ile Ala Gly Val Val Glu Met Lys
865                 870                 875                 880
Met Leu Ser Gly Gln Ala Leu Lys Asp Lys Lys Glu Leu Glu Gly Ala
            885                 890                 895
Gly Lys Ile Ala Thr Glu Ala Ile Glu Asn Phe Arg Thr Val Val Ser
        900                 905                 910
Leu Thr Gln Glu Gln Lys Phe Glu His Met Tyr Asp Gln Ser Leu Gln
        915                 920                 925
Val Pro Tyr Arg Asn Ser Leu Arg Lys Ala His Ile Phe Gly Ile Thr
        930                 935                 940
Phe Ser Phe Thr Gln Ala Met Met Tyr Phe Ser Tyr Ala Gly Cys Phe
945                 950                 955                 960
Arg Phe Gly Ala Tyr Leu Val Ala His Ser Leu Met Ser Phe Glu Asp
                965                 970                 975
Val Leu Leu Val Phe Ser Ala Val Phe Gly Ala Met Ala Val Gly
            980                 985                 990
Gln Val Ser Ser Phe Ala Pro Asp Tyr Ala Lys Ala Lys Val Ser Ala
        995                 1000                1005
Ala His Ile Ile Met Ile Ile Glu Lys Thr Pro Leu Ile Asp Ser
    1010                1015                1020
Tyr Ser Thr Glu Gly Leu Lys Pro Asn Thr Leu Glu Gly Asn Val
    1025                1030                1035
Thr Phe Asn Glu Val Val Phe Asn Tyr Pro Thr Arg Leu Asp Ile
    1040                1045                1050
Pro Val Leu Gln Gly Leu Ser Leu Glu Val Lys Lys Gly Gln Thr
    1055                1060                1065
Leu Ala Leu Val Gly Ser Ser Gly Cys Gly Lys Ser Thr Val Val
    1070                1075                1080
Gln Leu Leu Glu Arg Phe Tyr Asp Pro Leu Ala Gly Lys Val Leu
    1085                1090                1095
Leu Asp Gly Lys Glu Ile Lys Gln Leu Asn Val Gln Trp Leu Arg
    1100                1105                1110
Ala His Leu Gly Ile Val Ser Gln Glu Pro Ile Leu Phe Asp Cys
    1115                1120                1125
Ser Ile Ser Glu Asn Ile Ala Tyr Gly Asp Asn Ser Arg Val Val
    1130                1135                1140
Ser Gln Glu Glu Ile Val Arg Ala Ala Lys Glu Ala Asn Ile His
    1145                1150                1155
Ala Phe Ile Glu Ser Leu Pro Asn Lys Tyr Ser Thr Arg Val Gly
    1160                1165                1170
Asp Lys Gly Thr Gln Leu Ser Gly Gly Gln Lys Gln Arg Ile Ala
    1175                1180                1185
Ile Ala Arg Ala Leu Val Arg Gln Pro His Ile Leu Leu Leu Asp
    1190                1195                1200
Glu Ala Thr Ser Ala Leu Asp Thr Glu Ser Glu Lys Val Val Gln
    1205                1210                1215
Glu Ala Leu Asp Lys Ala Arg Glu Gly Arg Thr Cys Ile Val Ile
    1220                1225                1230
Ala His Arg Leu Ser Thr Ile Gln Asn Ala Asp Leu Ile Val Val
```

-continued

```
              1235                1240                1245

Phe Gln  Asn Gly Arg Val Lys  Glu His Gly Thr His  Gln Gln Leu
         1250                1255                1260

Leu Ala  Gln Lys Gly Ile Tyr  Phe Ser Met Val Ser  Val Gln Ala
    1265                1270                1275

Gly Ala  Lys Arg Gln
    1280

<210> SEQ ID NO 3
<211> LENGTH: 1280
<212> TYPE: PRT
<213> ORGANISM: Macaca fascicularis

<400> SEQUENCE: 3

Met Asp Leu Glu Gly Asp Arg Asn Gly Gly Ala Glu Lys Lys Asn Phe
1               5                   10                  15

Phe Lys Leu Asn Asn Lys Ser Lys Asp Lys Lys Glu Arg Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Asp Met Thr Asp Thr Phe Ala
65                  70                  75                  80

Asn Ala Gly Asn Leu Gly Asp Leu Gly Ala Leu Leu Thr Asn Ser Ser
                85                  90                  95

Asn Ile Thr Asp Thr Val Pro Val Met Asn Leu Glu Glu Asp Met Thr
            100                 105                 110

Arg Tyr Ala Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320
```

```
Val Leu Ser Lys Glu Tyr Ser Ile Gly Gln Val Leu Thr Val Phe
            325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Phe Glu Ile Phe Lys Ile
            355                 360                 365

Ile Asp Asn Lys Pro Ser Ile Asp Ser Tyr Ser Lys Ser Gly His Lys
        370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
            435                 440                 445

Gly Met Val Ser Val Asp Gly Gln Asp Ile Arg Thr Ile Asn Val Arg
        450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asp Val Thr
                485                 490                 495

Met Asp Glu Ile Glu Lys Ala Val Lys Glu Ala Asn Ala Tyr Asp Phe
            500                 505                 510

Ile Met Lys Leu Pro Gln Lys Phe Asp Thr Leu Val Gly Glu Arg Gly
            515                 520                 525

Ala Gln Leu Ser Gly Gly Gln Lys Gln Arg Ile Ala Ile Ala Arg Ala
            530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
            595                 600                 605

Lys Gly Asn His Asp Glu Leu Met Lys Glu Lys Gly Ile Tyr Phe Lys
            610                 615                 620

Leu Val Thr Met Gln Thr Ala Gly Asn Glu Ile Glu Leu Glu Asn Ala
625                 630                 635                 640

Ala Asp Glu Ser Lys Ser Glu Ile Asp Thr Leu Glu Met Ser Ser His
                645                 650                 655

Asp Ser Gly Ser Ser Leu Ile Arg Lys Arg Ser Thr Arg Arg Ser Val
            660                 665                 670

Arg Gly Ser Gln Gly Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
            690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Val Ile Phe Ser Lys Ile Ile
                725                 730                 735

Gly Ile Phe Thr Arg Asn Asp Asp Ala Glu Thr Lys Arg Gln Asn Ser
```

-continued

```
                740                 745                 750
Asn Leu Phe Ser Leu Phe Leu Val Leu Gly Ile Val Ser Phe Ile
            755                 760                 765
Thr Phe Phe Leu Gln Gly Phe Thr Phe Gly Lys Ala Gly Glu Ile Leu
770                 775                 780
Thr Lys Arg Leu Arg Tyr Met Val Phe Arg Ser Met Leu Arg Gln Asp
785                 790                 795                 800
Val Ser Trp Phe Asp Asp Pro Lys Asn Thr Thr Gly Ala Leu Thr Thr
                805                 810                 815
Arg Leu Ala Asn Asp Ala Ala Gln Val Lys Gly Ala Ile Gly Ser Arg
            820                 825                 830
Leu Ala Ile Ile Thr Gln Asn Ile Ala Asn Leu Gly Thr Gly Ile Ile
            835                 840                 845
Ile Ser Leu Ile Tyr Gly Trp Gln Leu Thr Leu Leu Leu Leu Ala Ile
            850                 855                 860
Val Pro Ile Ile Ala Ile Ala Gly Val Val Glu Met Lys Met Leu Ser
865                 870                 875                 880
Gly Gln Ala Leu Lys Asp Lys Lys Glu Leu Glu Gly Ala Gly Lys Ile
                885                 890                 895
Ala Thr Glu Ala Ile Glu Asn Phe Arg Thr Val Val Ser Leu Thr Gln
                900                 905                 910
Glu Gln Lys Phe Glu His Met Tyr Asp Gln Ser Leu Gln Val Pro Tyr
            915                 920                 925
Arg Asn Ser Leu Arg Lys Ala His Ile Phe Gly Ile Thr Phe Ser Phe
            930                 935                 940
Thr Gln Ala Met Met Tyr Phe Ser Tyr Ala Gly Cys Phe Arg Phe Gly
945                 950                 955                 960
Ala Tyr Leu Val Ala His Ser Leu Met Ser Phe Glu Asp Val Leu Leu
                965                 970                 975
Val Phe Ser Ala Val Val Phe Gly Ala Met Ala Val Gly Gln Val Ser
                980                 985                 990
Ser Phe Ala Pro Asp Tyr Ala Lys Ala Lys Val Ser Ala Ala His Ile
            995                 1000                1005
Ile Met Ile Ile Glu Lys Thr Pro Leu Ile Asp Ser Tyr Ser Thr
1010                1015                1020
Glu Gly Leu Lys Pro Asn Thr Leu Glu Gly Asn Val Thr Phe Asn
1025                1030                1035
Glu Val Val Phe Asn Tyr Pro Thr Arg Leu Asp Ile Pro Val Leu
1040                1045                1050
Gln Gly Leu Ser Leu Glu Val Lys Lys Gly Gln Thr Leu Ala Leu
1055                1060                1065
Val Gly Ser Ser Gly Cys Gly Lys Ser Thr Val Val Gln Leu Leu
1070                1075                1080
Glu Arg Phe Tyr Asp Pro Leu Ala Gly Lys Val Leu Leu Asp Gly
1085                1090                1095
Lys Glu Ile Lys Gln Leu Asn Val Gln Trp Leu Arg Ala His Leu
1100                1105                1110
Gly Ile Val Ser Gln Glu Pro Ile Leu Phe Asp Cys Ser Ile Ser
1115                1120                1125
Glu Asn Ile Ala Tyr Gly Asp Asn Ser Arg Val Val Ser Gln Glu
1130                1135                1140
Glu Ile Val Arg Ala Ala Lys Glu Ala Asn Ile His Ala Phe Ile
1145                1150                1155
```

```
Glu Ser Leu Pro Asn Lys Tyr Ser Thr Arg Val Gly Asp Lys Gly
    1160                1165                1170

Thr Gln Leu Ser Gly Gly Gln Lys Gln Arg Ile Ala Ile Ala Arg
    1175                1180                1185

Ala Leu Val Arg Gln Pro His Ile Leu Leu Leu Asp Glu Ala Thr
    1190                1195                1200

Ser Ala Leu Asp Thr Glu Ser Glu Lys Val Val Gln Glu Ala Leu
    1205                1210                1215

Asp Lys Ala Arg Glu Gly Arg Thr Cys Ile Val Ile Ala His Arg
    1220                1225                1230

Leu Ser Thr Ile Gln Asn Ala Asp Leu Ile Val Val Phe Gln Asn
    1235                1240                1245

Gly Arg Val Lys Glu His Gly Thr His Gln Gln Leu Leu Ala Gln
    1250                1255                1260

Lys Gly Ile Tyr Phe Ser Met Val Ser Val Gln Ala Gly Ala Lys
    1265                1270                1275

Arg Gln
    1280

<210> SEQ ID NO 4
<211> LENGTH: 1283
<212> TYPE: PRT
<213> ORGANISM: Macaca fascicularis

<400> SEQUENCE: 4

Met Asp Leu Glu Gly Asp Arg Asn Gly Gly Ala Glu Lys Lys Asn Phe
1               5                   10                  15

Phe Lys Leu Asn Asn Lys Ser Lys Lys Asp Lys Glu Arg Lys Pro
            20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
    50                  55                  60

Leu Pro Leu Met Met Leu Val Phe Gly Asp Met Thr Asp Thr Phe Ala
65                  70                  75                  80

Asn Ala Gly Asn Leu Gly Asp Leu Gly Ala Leu Leu Phe Asn Asn Thr
                85                  90                  95

Asn Ser Ser Asn Ile Thr Asp Thr Val Pro Val Met Asn Leu Glu Glu
            100                 105                 110

Asp Met Thr Arg Tyr Ala Tyr Tyr Tyr Ser Gly Ile Gly Ala Gly Val
            115                 120                 125

Leu Val Ala Ala Tyr Ile Gln Val Ser Phe Trp Cys Leu Ala Ala Gly
    130                 135                 140

Arg Gln Ile His Lys Ile Arg Lys Gln Phe Phe His Ala Ile Met Arg
145                 150                 155                 160

Gln Glu Ile Gly Trp Phe Asp Val His Asp Val Gly Glu Leu Asn Thr
                165                 170                 175

Arg Leu Thr Asp Asp Val Ser Lys Ile Asn Glu Gly Ile Gly Asp Lys
            180                 185                 190

Ile Gly Met Phe Phe Gln Ser Met Ala Thr Phe Phe Thr Gly Phe Ile
            195                 200                 205

Val Gly Phe Thr Arg Gly Trp Lys Leu Thr Leu Val Ile Leu Ala Ile
    210                 215                 220

Ser Pro Val Leu Gly Leu Ser Ala Ala Val Trp Ala Lys Ile Leu Ser
```

-continued

```
            225                 230                 235                 240

Ser Phe Thr Asp Lys Glu Leu Leu Ala Tyr Ala Lys Ala Gly Ala Val
                245                 250                 255

Ala Glu Glu Val Leu Ala Ala Ile Arg Thr Val Ile Ala Phe Gly Gly
            260                 265                 270

Gln Lys Lys Glu Leu Glu Arg Tyr Asn Lys Asn Leu Glu Glu Ala Lys
        275                 280                 285

Arg Ile Gly Ile Lys Lys Ala Ile Thr Ala Asn Ile Ser Ile Gly Ala
    290                 295                 300

Ala Phe Leu Leu Ile Tyr Ala Ser Tyr Ala Leu Ala Phe Trp Tyr Gly
305                 310                 315                 320

Thr Thr Leu Val Leu Ser Lys Glu Tyr Ser Ile Gly Gln Val Leu Thr
                325                 330                 335

Val Phe Phe Ser Val Leu Ile Gly Ala Phe Ser Val Gly Gln Ala Ser
                340                 345                 350

Pro Ser Ile Glu Ala Phe Ala Asn Ala Arg Gly Ala Ala Phe Glu Ile
        355                 360                 365

Phe Lys Ile Ile Asp Asn Lys Pro Ser Ile Asp Ser Tyr Ser Lys Ser
    370                 375                 380

Gly His Lys Pro Asp Asn Ile Lys Gly Asn Leu Glu Phe Arg Asn Val
385                 390                 395                 400

His Phe Ser Tyr Pro Ser Arg Lys Glu Val Lys Ile Leu Lys Gly Leu
                405                 410                 415

Asn Leu Lys Val Gln Ser Gly Gln Thr Val Ala Leu Val Gly Asn Ser
            420                 425                 430

Gly Cys Gly Lys Ser Thr Thr Val Gln Leu Met Gln Arg Leu Tyr Asp
        435                 440                 445

Pro Thr Glu Gly Met Val Ser Val Asp Gly Gln Asp Ile Arg Thr Ile
    450                 455                 460

Asn Val Arg Phe Leu Arg Glu Ile Ile Gly Val Val Ser Gln Glu Pro
465                 470                 475                 480

Val Leu Phe Ala Thr Thr Ile Ala Glu Asn Ile Arg Tyr Gly Arg Glu
                485                 490                 495

Asp Val Thr Met Asp Glu Ile Glu Lys Ala Val Lys Glu Ala Asn Ala
            500                 505                 510

Tyr Asp Phe Ile Met Lys Leu Pro Gln Lys Phe Asp Thr Leu Val Gly
        515                 520                 525

Glu Arg Gly Ala Gln Leu Ser Gly Gly Gln Lys Gln Arg Ile Ala Ile
    530                 535                 540

Ala Arg Ala Leu Val Arg Asn Pro Lys Ile Leu Leu Leu Asp Glu Ala
545                 550                 555                 560

Thr Ser Ala Leu Asp Thr Glu Ser Glu Ala Val Val Gln Val Ala Leu
                565                 570                 575

Asp Lys Ala Arg Lys Gly Arg Thr Thr Ile Val Ile Ala His Arg Leu
            580                 585                 590

Ser Thr Val Arg Asn Ala Asp Val Ile Ala Gly Phe Asp Asp Gly Val
        595                 600                 605

Ile Val Glu Lys Gly Asn His Asp Glu Leu Met Lys Glu Lys Gly Ile
    610                 615                 620

Tyr Phe Lys Leu Val Thr Met Gln Thr Ala Gly Asn Glu Ile Glu Leu
625                 630                 635                 640

Glu Asn Ala Ala Asp Glu Ser Lys Ser Glu Ile Asp Thr Leu Glu Met
                645                 650                 655
```

-continued

```
Ser Ser His Asp Ser Gly Ser Ser Leu Ile Arg Lys Arg Ser Thr Arg
            660                 665                 670

Arg Ser Val Arg Gly Ser Gln Gly Gln Asp Arg Lys Leu Ser Thr Lys
            675                 680                 685

Glu Ala Leu Asp Glu Ser Ile Pro Pro Val Ser Phe Trp Arg Ile Met
            690                 695                 700

Lys Leu Asn Leu Thr Glu Trp Pro Tyr Phe Val Gly Val Phe Cys
705                 710                 715                 720

Ala Ile Ile Asn Gly Gly Leu Gln Pro Ala Phe Ala Val Ile Phe Ser
                    725                 730                 735

Lys Ile Ile Gly Ile Phe Thr Arg Asn Asp Asp Ala Glu Thr Lys Arg
                    740                 745                 750

Gln Asn Ser Asn Leu Phe Ser Leu Leu Phe Leu Val Leu Gly Ile Val
                    755                 760                 765

Ser Phe Ile Thr Phe Phe Leu Gln Gly Phe Thr Phe Gly Lys Ala Gly
            770                 775                 780

Glu Ile Leu Thr Lys Arg Leu Arg Tyr Met Val Phe Arg Ser Met Leu
785                 790                 795                 800

Arg Gln Asp Val Ser Trp Phe Asp Asp Pro Lys Asn Thr Thr Gly Ala
                    805                 810                 815

Leu Thr Thr Arg Leu Ala Asn Asp Ala Ala Gln Val Lys Gly Ala Ile
                    820                 825                 830

Gly Ser Arg Leu Ala Ile Ile Thr Gln Asn Ile Ala Asn Leu Gly Thr
            835                 840                 845

Gly Ile Ile Ile Ser Leu Ile Tyr Gly Trp Gln Leu Thr Leu Leu Leu
850                 855                 860

Leu Ala Ile Val Pro Ile Ile Ala Ile Ala Gly Val Val Glu Met Lys
865                 870                 875                 880

Met Leu Ser Gly Gln Ala Leu Lys Asp Lys Lys Glu Leu Glu Gly Ala
                    885                 890                 895

Gly Lys Ile Ala Thr Glu Ala Ile Glu Asn Phe Arg Thr Val Val Ser
            900                 905                 910

Leu Thr Gln Glu Gln Lys Phe Glu His Met Tyr Asp Gln Ser Leu Gln
            915                 920                 925

Val Pro Tyr Arg Asn Ser Leu Arg Lys Ala His Ile Phe Gly Ile Thr
            930                 935                 940

Phe Ser Phe Thr Gln Ala Met Met Tyr Phe Ser Tyr Ala Gly Cys Phe
945                 950                 955                 960

Arg Phe Gly Ala Tyr Leu Val Ala His Ser Leu Met Ser Phe Glu Asp
                    965                 970                 975

Val Leu Leu Val Phe Ser Ala Val Val Phe Gly Ala Met Ala Val Gly
                    980                 985                 990

Gln Val Ser Ser Phe Ala Pro Asp Tyr Ala Lys Ala Lys Val Ser Ala
            995                 1000                1005

Ala His Ile Ile Met Ile Ile Glu Lys Thr Pro Leu Ile Asp Ser
    1010                1015                1020

Tyr Ser Thr Glu Gly Leu Lys Pro Asn Thr Leu Glu Gly Asn Val
    1025                1030                1035

Thr Phe Asn Glu Val Val Phe Asn Tyr Pro Thr Arg Leu Asp Ile
    1040                1045                1050

Pro Val Leu Gln Gly Leu Ser Leu Glu Val Lys Lys Gly Gln Thr
    1055                1060                1065
```

```
Leu Ala Leu Val Gly Ser Ser Gly Cys Gly Lys Ser Thr Val Val
    1070             1075             1080

Gln Leu Leu Glu Arg Phe Tyr Asp Pro Leu Ala Gly Lys Val Leu
    1085             1090             1095

Leu Asp Gly Lys Glu Ile Lys Gln Leu Asn Val Gln Trp Leu Arg
    1100             1105             1110

Ala His Leu Gly Ile Val Ser Gln Glu Pro Ile Leu Phe Asp Cys
    1115             1120             1125

Ser Ile Ser Glu Asn Ile Ala Tyr Gly Asp Asn Ser Arg Val Val
    1130             1135             1140

Ser Gln Glu Glu Ile Val Arg Ala Ala Lys Glu Ala Asn Ile His
    1145             1150             1155

Ala Phe Ile Glu Ser Leu Pro Asn Lys Tyr Ser Thr Arg Val Gly
    1160             1165             1170

Asp Lys Gly Thr Gln Leu Ser Gly Gly Gln Lys Gln Arg Ile Ala
    1175             1180             1185

Ile Ala Arg Ala Leu Val Arg Gln Pro His Ile Leu Leu Leu Asp
    1190             1195             1200

Glu Ala Thr Ser Ala Leu Asp Thr Glu Ser Glu Lys Val Val Gln
    1205             1210             1215

Glu Ala Leu Asp Lys Ala Arg Glu Gly Arg Thr Cys Ile Val Ile
    1220             1225             1230

Ala His Arg Leu Ser Thr Ile Gln Asn Ala Asp Leu Ile Val Val
    1235             1240             1245

Phe Gln Asn Gly Arg Val Lys Glu His Gly Thr His Gln Gln Leu
    1250             1255             1260

Leu Ala Gln Lys Gly Ile Tyr Phe Ser Met Val Ser Val Gln Ala
    1265             1270             1275

Gly Ala Lys Arg Gln
    1280

<210> SEQ ID NO 5
<211> LENGTH: 1280
<212> TYPE: PRT
<213> ORGANISM: Homo sapiens

<400> SEQUENCE: 5

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140
```

```
His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
            165                 170                 175

Asp Asp Val Ser Lys Ile Asn Glu Val Ile Gly Asp Lys Ile Gly Met
                180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
                275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
                340                 345                 350

Glu Ala Phe Ala Asn Ala Arg Gly Ala Ala Tyr Glu Ile Phe Lys Ile
                355                 360                 365

Ile Asp Asn Lys Pro Ser Ile Asp Ser Tyr Ser Lys Ser Gly His Lys
370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
                420                 425                 430

Lys Ser Thr Thr Val Gln Leu Met Gln Arg Leu Tyr Asp Pro Thr Glu
                435                 440                 445

Gly Met Val Ser Val Asp Gly Gln Asp Ile Arg Thr Ile Asn Val Arg
450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
                500                 505                 510

Ile Met Lys Leu Pro His Lys Phe Asp Thr Leu Val Gly Glu Arg Gly
                515                 520                 525

Ala Gln Leu Ser Gly Gly Gln Lys Gln Arg Ile Ala Ile Ala Arg Ala
                530                 535                 540

Leu Val Arg Asn Pro Lys Ile Leu Leu Leu Asp Glu Ala Thr Ser Ala
545                 550                 555                 560
```

-continued

```
Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
        675                 680                 685

Asp Glu Ser Ile Pro Pro Val Ser Phe Trp Arg Ile Met Lys Leu Asn
    690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
    930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
```

```
                980             985             990
Ser Phe Ala Pro Asp Tyr Ala Lys Ala Lys Ile Ser Ala Ala His Ile
            995             1000            1005

Ile Met Ile Ile Glu Lys Thr Pro Leu Ile Asp Ser Tyr Ser Thr
    1010            1015            1020

Glu Gly Leu Met Pro Asn Thr Leu Glu Gly Asn Val Thr Phe Gly
    1025            1030            1035

Glu Val Val Phe Asn Tyr Pro Thr Arg Pro Asp Ile Pro Val Leu
    1040            1045            1050

Gln Gly Leu Ser Leu Glu Val Lys Lys Gly Gln Thr Leu Ala Leu
    1055            1060            1065

Val Gly Ser Ser Gly Cys Gly Lys Ser Thr Val Val Gln Leu Leu
    1070            1075            1080

Glu Arg Phe Tyr Asp Pro Leu Ala Gly Lys Val Leu Leu Asp Gly
    1085            1090            1095

Lys Glu Ile Lys Arg Leu Asn Val Gln Trp Leu Arg Ala His Leu
    1100            1105            1110

Gly Ile Val Ser Gln Glu Pro Ile Leu Phe Asp Cys Ser Ile Ala
    1115            1120            1125

Glu Asn Ile Ala Tyr Gly Asp Asn Ser Arg Val Val Ser Gln Glu
    1130            1135            1140

Glu Ile Val Arg Ala Ala Lys Glu Ala Asn Ile His Ala Phe Ile
    1145            1150            1155

Glu Ser Leu Pro Asn Lys Tyr Ser Thr Lys Val Gly Asp Lys Gly
    1160            1165            1170

Thr Gln Leu Ser Gly Gly Gln Lys Gln Arg Ile Ala Ile Ala Arg
    1175            1180            1185

Ala Leu Val Arg Gln Pro His Ile Leu Leu Leu Asp Glu Ala Thr
    1190            1195            1200

Ser Ala Leu Asp Thr Glu Ser Glu Lys Val Val Gln Glu Ala Leu
    1205            1210            1215

Asp Lys Ala Arg Glu Gly Arg Thr Cys Ile Val Ile Ala His Arg
    1220            1225            1230

Leu Ser Thr Ile Gln Asn Ala Asp Leu Ile Val Val Phe Gln Asn
    1235            1240            1245

Gly Arg Val Lys Glu His Gly Thr His Gln Gln Leu Leu Ala Gln
    1250            1255            1260

Lys Gly Ile Tyr Phe Ser Met Val Ser Val Gln Ala Gly Thr Lys
    1265            1270            1275

Arg Gln
    1280

<210> SEQ ID NO 6
<211> LENGTH: 1279
<212> TYPE: PRT
<213> ORGANISM: Homo sapiens

<400> SEQUENCE: 6

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Lys Glu Lys Lys Pro
            20                  25                  30

Thr Val Ser Val Phe Ser Met Phe Arg Tyr Ser Asn Trp Leu Asp Lys
        35                  40                  45
```

```
Leu Tyr Met Val Val Gly Thr Leu Ala Ala Ile Ile His Gly Ala Gly
 50                  55                  60

Leu Pro Leu Met Met Leu Val Phe Gly Glu Met Thr Asp Ile Phe Ala
 65                  70                  75                  80

Asn Ala Gly Asn Leu Glu Asp Leu Met Ser Asn Ile Thr Asn Arg Ser
                 85                  90                  95

Asp Ile Asn Asp Thr Gly Phe Phe Met Asn Leu Glu Glu Asp Met Thr
            100                 105                 110

Arg Tyr Ala Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                    165                 170                 175

Asp Asp Val Ser Lys Ile Asn Glu Gly Ile Gly Asp Lys Ile Gly Met
                180                 185                 190

Phe Phe Gln Ser Met Ala Thr Phe Phe Thr Gly Phe Ile Val Gly Phe
            195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                    245                 250                 255

Val Leu Ala Ala Ile Arg Thr Val Ile Ala Phe Gly Gly Gln Lys Lys
                260                 265                 270

Glu Leu Glu Arg Tyr Asn Lys Asn Leu Glu Glu Ala Lys Arg Ile Gly
            275                 280                 285

Ile Lys Lys Ala Ile Thr Ala Asn Ile Ser Ile Gly Ala Ala Phe Leu
290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Ser
                    325                 330                 335

Val Leu Ile Gly Ala Phe Ser Val Gly Gln Ala Ser Pro Ser Ile Glu
                340                 345                 350

Ala Phe Ala Asn Ala Arg Gly Ala Ala Tyr Glu Ile Phe Lys Ile Ile
            355                 360                 365

Asp Asn Lys Pro Ser Ile Asp Ser Tyr Ser Lys Ser Gly His Lys Pro
370                 375                 380

Asp Asn Ile Lys Gly Asn Leu Glu Phe Arg Asn Val His Phe Ser Tyr
385                 390                 395                 400

Pro Ser Arg Lys Glu Val Lys Ile Leu Lys Gly Leu Asn Leu Lys Val
                405                 410                 415

Gln Ser Gly Gln Thr Val Ala Leu Val Gly Asn Ser Gly Cys Gly Lys
            420                 425                 430

Ser Thr Thr Val Gln Leu Met Gln Arg Leu Tyr Asp Pro Thr Glu Gly
        435                 440                 445

Met Val Ser Val Asp Gly Gln Asp Ile Arg Thr Ile Asn Val Arg Phe
450                 455                 460

Leu Arg Glu Ile Ile Gly Val Val Ser Gln Glu Pro Val Leu Phe Ala
```

-continued

```
            465                 470                 475                 480
Thr Thr Ile Ala Glu Asn Ile Arg Tyr Gly Arg Glu Asn Val Thr Met
                    485                 490                 495
Asp Glu Ile Glu Lys Ala Val Lys Glu Ala Asn Ala Tyr Asp Phe Ile
                500                 505                 510
Met Lys Leu Pro His Lys Phe Asp Thr Leu Val Gly Glu Arg Gly Ala
            515                 520                 525
Gln Leu Ser Gly Gly Gln Lys Gln Arg Ile Ala Ile Ala Arg Ala Leu
        530                 535                 540
Val Arg Asn Pro Lys Ile Leu Leu Leu Asp Glu Ala Thr Ser Ala Leu
545                 550                 555                 560
Asp Thr Glu Ser Glu Ala Val Val Gln Val Ala Leu Asp Lys Ala Arg
                565                 570                 575
Lys Gly Arg Thr Thr Ile Val Ile Ala His Arg Leu Ser Thr Val Arg
                580                 585                 590
Asn Ala Asp Val Ile Ala Gly Phe Asp Asp Gly Val Ile Val Glu Lys
            595                 600                 605
Gly Asn His Asp Glu Leu Met Lys Glu Lys Gly Ile Tyr Phe Lys Leu
        610                 615                 620
Val Thr Met Gln Thr Ala Gly Asn Glu Val Glu Leu Glu Asn Ala Ala
625                 630                 635                 640
Asp Glu Ser Lys Ser Glu Ile Asp Ala Leu Glu Met Ser Ser Asn Asp
                645                 650                 655
Ser Arg Ser Ser Leu Ile Arg Lys Arg Ser Thr Arg Arg Ser Val Arg
                660                 665                 670
Gly Ser Gln Ala Gln Asp Arg Lys Leu Ser Thr Lys Glu Ala Leu Asp
            675                 680                 685
Glu Ser Ile Pro Pro Val Ser Phe Trp Arg Ile Met Lys Leu Asn Leu
        690                 695                 700
Thr Glu Trp Pro Tyr Phe Val Val Gly Val Phe Cys Ala Ile Ile Asn
705                 710                 715                 720
Gly Gly Leu Gln Pro Ala Phe Ala Ile Ile Phe Ser Lys Ile Ile Gly
                725                 730                 735
Val Phe Thr Arg Ile Asp Asp Pro Glu Thr Lys Arg Gln Asn Ser Asn
                740                 745                 750
Leu Phe Ser Leu Leu Phe Leu Ala Leu Gly Ile Ile Ser Phe Ile Thr
            755                 760                 765
Phe Phe Leu Gln Gly Phe Thr Phe Gly Lys Ala Gly Glu Ile Leu Thr
        770                 775                 780
Lys Arg Leu Arg Tyr Met Val Phe Arg Ser Met Leu Arg Gln Asp Val
785                 790                 795                 800
Ser Trp Phe Asp Asp Pro Lys Asn Thr Thr Gly Ala Leu Thr Thr Arg
                805                 810                 815
Leu Ala Asn Asp Ala Ala Gln Val Lys Gly Ala Ile Gly Ser Arg Leu
            820                 825                 830
Ala Val Ile Thr Gln Asn Ile Ala Asn Leu Gly Thr Gly Ile Ile Ile
        835                 840                 845
Ser Phe Ile Tyr Gly Trp Gln Leu Thr Leu Leu Leu Ala Ile Val
        850                 855                 860
Pro Ile Ile Ala Ile Ala Gly Val Val Glu Met Lys Met Leu Ser Gly
865                 870                 875                 880
Gln Ala Leu Lys Asp Lys Lys Glu Leu Glu Gly Ala Gly Lys Ile Ala
                885                 890                 895
```

-continued

```
Thr Glu Ala Ile Glu Asn Phe Arg Thr Val Val Ser Leu Thr Gln Glu
        900                 905                 910

Gln Lys Phe Glu His Met Tyr Ala Gln Ser Leu Gln Val Pro Tyr Arg
        915                 920                 925

Asn Ser Leu Arg Lys Ala His Ile Phe Gly Ile Thr Phe Ser Phe Thr
        930                 935                 940

Gln Ala Met Met Tyr Phe Ser Tyr Ala Gly Cys Phe Arg Phe Gly Ala
945                 950                 955                 960

Tyr Leu Val Ala His Lys Leu Met Ser Phe Glu Asp Val Leu Leu Val
                965                 970                 975

Phe Ser Ala Val Val Phe Gly Ala Met Ala Val Gly Gln Val Ser Ser
        980                 985                 990

Phe Ala Pro Asp Tyr Ala Lys Ala Lys Ile Ser Ala Ala His Ile Ile
        995                 1000                1005

Met Ile Ile Glu Lys Thr Pro Leu Ile Asp Ser Tyr Ser Thr Glu
        1010                1015                1020

Gly Leu Met Pro Asn Thr Leu Glu Gly Asn Val Thr Phe Gly Glu
        1025                1030                1035

Val Val Phe Asn Tyr Pro Thr Arg Pro Asp Ile Pro Val Leu Gln
        1040                1045                1050

Gly Leu Ser Leu Glu Val Lys Lys Gly Gln Thr Leu Ala Leu Val
        1055                1060                1065

Gly Ser Ser Gly Cys Gly Lys Ser Thr Val Val Gln Leu Leu Glu
        1070                1075                1080

Arg Phe Tyr Asp Pro Leu Ala Gly Lys Val Leu Leu Asp Gly Lys
        1085                1090                1095

Glu Ile Lys Arg Leu Asn Val Gln Trp Leu Arg Ala His Leu Gly
        1100                1105                1110

Ile Val Ser Gln Glu Pro Ile Leu Phe Asp Cys Ser Ile Ala Glu
        1115                1120                1125

Asn Ile Ala Tyr Gly Asp Asn Ser Arg Val Val Ser Gln Glu Glu
        1130                1135                1140

Ile Val Arg Ala Ala Lys Glu Ala Asn Ile His Ala Phe Ile Glu
        1145                1150                1155

Ser Leu Pro Asn Lys Tyr Ser Thr Lys Val Gly Asp Lys Gly Thr
        1160                1165                1170

Gln Leu Ser Gly Gly Gln Lys Gln Arg Ile Ala Ile Ala Arg Ala
        1175                1180                1185

Leu Val Arg Gln Pro His Ile Leu Leu Leu Asp Glu Ala Thr Ser
        1190                1195                1200

Ala Leu Asp Thr Glu Ser Glu Lys Val Val Gln Glu Ala Leu Asp
        1205                1210                1215

Lys Ala Arg Glu Gly Arg Thr Cys Ile Val Ile Ala His Arg Leu
        1220                1225                1230

Ser Thr Ile Gln Asn Ala Asp Leu Ile Val Val Phe Gln Asn Gly
        1235                1240                1245

Arg Val Lys Glu His Gly Thr His Gln Gln Leu Leu Ala Gln Lys
        1250                1255                1260

Gly Ile Tyr Phe Ser Met Val Ser Val Gln Ala Gly Thr Lys Arg
        1265                1270                1275

Gln
```

-continued

<210> SEQ ID NO 7
<211> LENGTH: 1281
<212> TYPE: PRT
<213> ORGANISM: Canis familiaris

<400> SEQUENCE: 7

```
Met Asp Pro Glu Gly Gly Arg Lys Gly Ser Ala Glu Lys Asn Phe Trp
1               5                   10                  15

Lys Met Gly Lys Lys Ser Lys Lys Asn Glu Lys Glu Lys Lys Pro
            20                  25                  30

Thr Val Ser Thr Phe Ala Met Phe Arg Tyr Ser Asn Trp Leu Asp Arg
            35                  40                  45

Leu Tyr Met Leu Val Gly Thr Met Ala Ala Ile Ile His Gly Ala Ala
    50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110

Met Thr Thr Tyr Ala Tyr Tyr Ser Gly Ile Gly Ala Gly Val Leu
            115                 120                 125

Val Ala Ala Tyr Ile Gln Val Ser Phe Trp Cys Leu Ala Ala Gly Arg
    130                 135                 140

Gln Ile Leu Lys Ile Arg Lys Gln Phe Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe His Ser Ile Ala Thr Phe Phe Thr Gly Phe Ile Val
        195                 200                 205

Gly Phe Thr Arg Gly Trp Lys Leu Thr Leu Val Ile Leu Ala Ile Ser
    210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
        275                 280                 285

Ile Gly Ile Lys Lys Ala Ile Thr Ala Asn Ile Ser Ile Gly Ala Ala
    290                 295                 300

Phe Leu Leu Ile Tyr Ala Ser Tyr Ala Leu Ala Phe Trp Tyr Gly Thr
305                 310                 315                 320

Ser Leu Val Leu Ser Ser Glu Tyr Ser Ile Gly Gln Val Leu Thr Val
                325                 330                 335

Phe Phe Ser Val Leu Ile Gly Ala Phe Ser Ile Gly Gln Ala Ser Pro
            340                 345                 350

Ser Ile Glu Ala Phe Ala Asn Ala Arg Gly Ala Ala Tyr Glu Ile Phe
        355                 360                 365

Lys Ile Ile Asp Asn Lys Pro Ser Ile Asp Ser Tyr Ser Lys Ser Gly
    370                 375                 380
```

-continued

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
            405                 410                 415

Leu Lys Val Gln Ser Gly Gln Thr Val Ala Leu Val Gly Asn Ser Gly
        420                 425                 430

Cys Gly Lys Ser Thr Thr Val Gln Leu Met Gln Arg Leu Tyr Asp Pro
    435                 440                 445

Thr Asp Gly Met Val Cys Ile Asp Gly Gln Asp Ile Arg Thr Ile Asn
    450                 455                 460

Val Arg His Leu Arg Glu Ile Thr Gly Val Val Ser Gln Glu Pro Val
465                 470                 475                 480

Leu Phe Ala Thr Thr Ile Ala Glu Asn Ile Arg Tyr Gly Arg Glu Asn
                485                 490                 495

Val Thr Met Asp Glu Ile Glu Lys Ala Val Lys Glu Ala Asn Ala Tyr
            500                 505                 510

Asp Phe Ile Met Lys Leu Pro Asn Lys Phe Asp Thr Leu Val Gly Glu
        515                 520                 525

Arg Gly Ala Gln Leu Ser Gly Gly Gln Lys Gln Arg Ile Ala Ile Ala
    530                 535                 540

Arg Ala Leu Val Arg Asn Pro Lys Ile Leu Leu Leu Asp Glu Ala Thr
545                 550                 555                 560

Ser Ala Leu Asp Thr Glu Ser Glu Ala Val Val Gln Val Ala Leu Asp
                565                 570                 575

Lys Ala Arg Lys Gly Arg Thr Thr Ile Val Ile Ala His Arg Leu Ser
            580                 585                 590

Thr Val Arg Asn Ala Asp Val Ile Ala Gly Phe Asp Asp Gly Val Ile
        595                 600                 605

Val Glu Lys Gly Asn His Asp Glu Leu Met Lys Glu Lys Gly Ile Tyr
    610                 615                 620

Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
                645                 650                 655

Pro Lys Asp Ser Gly Ser Ser Leu Ile Lys Arg Arg Ser Thr Arg Arg
            660                 665                 670

Ser Ile His Ala Pro Gln Gly Gln Asp Arg Lys Leu Gly Thr Lys Glu
        675                 680                 685

Asp Leu Asn Glu Asn Val Pro Pro Val Ser Phe Trp Arg Ile Leu Lys
    690                 695                 700

Leu Asn Ser Thr Glu Trp Pro Tyr Phe Val Val Gly Ile Phe Cys Ala
705                 710                 715                 720

Ile Ile Asn Gly Gly Leu Gln Pro Ala Phe Ser Ile Ile Phe Ser Arg
                725                 730                 735

Ile Ile Gly Ile Phe Thr Arg Asp Glu Asp Pro Glu Thr Lys Arg Gln
            740                 745                 750

Asn Ser Asn Met Phe Ser Val Leu Phe Leu Val Leu Gly Ile Ile Ser
        755                 760                 765

Phe Ile Thr Phe Phe Leu Gln Gly Phe Thr Phe Gly Lys Ala Gly Glu
    770                 775                 780

Ile Leu Thr Lys Arg Leu Arg Tyr Met Val Phe Arg Ser Met Leu Arg
785                 790                 795                 800

Gln Asp Val Ser Trp Phe Asp Asp Pro Lys Asn Thr Thr Gly Ala Leu

-continued

```
                805                 810                 815
Thr Thr Arg Leu Ala Asn Asp Ala Ala Gln Val Lys Gly Ala Ile Gly
            820                 825                 830
Ser Arg Leu Ala Val Ile Thr Gln Asn Ile Ala Asn Leu Gly Thr Gly
            835                 840                 845
Ile Ile Ile Ser Leu Ile Tyr Gly Trp Gln Leu Thr Leu Leu Leu Leu
            850                 855                 860
Ala Ile Val Pro Ile Ile Ala Ile Ala Gly Val Val Glu Met Lys Met
865                 870                 875                 880
Leu Ser Gly Gln Ala Leu Lys Asp Lys Lys Glu Leu Glu Gly Ala Gly
            885                 890                 895
Lys Ile Ala Thr Glu Ala Ile Glu Asn Phe Arg Thr Val Val Ser Leu
            900                 905                 910
Thr Arg Glu Gln Lys Phe Glu Tyr Met Tyr Ala Gln Ser Leu Gln Val
            915                 920                 925
Pro Tyr Arg Asn Ser Leu Arg Lys Ala His Ile Phe Gly Val Ser Phe
            930                 935                 940
Ser Ile Thr Gln Ala Met Met Tyr Phe Ser Tyr Ala Gly Cys Phe Arg
945                 950                 955                 960
Phe Gly Ala Tyr Leu Val Ala Asn Glu Phe Met Asn Phe Gln Asp Val
            965                 970                 975
Leu Leu Val Phe Ser Ala Ile Val Phe Gly Ala Met Ala Val Gly Gln
            980                 985                 990
Val Ser Ser Phe Ala Pro Asp Tyr Ala Lys Ala Lys Val Ser Ala Ala
            995                 1000                1005
His Val Ile Met Ile Ile Glu Lys Ser Pro Leu Ile Asp Ser Tyr
            1010                1015                1020
Ser Pro His Gly Leu Lys Pro Asn Thr Leu Glu Gly Asn Val Thr
            1025                1030                1035
Phe Asn Glu Val Val Phe Asn Tyr Pro Thr Arg Pro Asp Ile Pro
            1040                1045                1050
Val Leu Gln Gly Leu Ser Leu Glu Val Lys Lys Gly Gln Thr Leu
            1055                1060                1065
Ala Leu Val Gly Ser Ser Gly Cys Gly Lys Ser Thr Val Val Gln
            1070                1075                1080
Leu Leu Glu Arg Phe Tyr Asp Pro Leu Ala Gly Ser Val Leu Ile
            1085                1090                1095
Asp Gly Lys Glu Ile Lys His Leu Asn Val Gln Trp Leu Arg Ala
            1100                1105                1110
His Leu Gly Ile Val Ser Gln Glu Pro Ile Leu Phe Asp Cys Ser
            1115                1120                1125
Ile Ala Glu Asn Ile Ala Tyr Gly Asp Asn Ser Arg Val Val Ser
            1130                1135                1140
His Glu Glu Ile Met Gln Ala Ala Lys Glu Ala Asn Ile His His
            1145                1150                1155
Phe Ile Glu Thr Leu Pro Glu Lys Tyr Asn Thr Arg Val Gly Asp
            1160                1165                1170
Lys Gly Thr Gln Leu Ser Gly Gly Gln Lys Gln Arg Ile Ala Ile
            1175                1180                1185
Ala Arg Ala Leu Val Arg Gln Pro His Ile Leu Leu Leu Asp Glu
            1190                1195                1200
Ala Thr Ser Ala Leu Asp Thr Glu Ser Glu Lys Val Val Gln Glu
            1205                1210                1215
```

```
Ala Leu Asp Lys Ala Arg Glu Gly Arg Thr Cys Ile Val Ile Ala
    1220                1225                1230

His Arg Leu Ser Thr Ile Gln Asn Ala Asp Leu Ile Val Val Phe
    1235                1240                1245

Gln Asn Gly Lys Val Lys Glu His Gly Thr His Gln Gln Leu Leu
    1250                1255                1260

Ala Gln Lys Gly Ile Tyr Phe Ser Met Val Ser Val Gln Ala Gly
    1265                1270                1275

Ala Lys Arg
    1280

<210> SEQ ID NO 8
<211> LENGTH: 1281
<212> TYPE: PRT
<213> ORGANISM: Canis familiaris

<400> SEQUENCE: 8

Met Asp Pro Glu Gly Gly Arg Lys Gly Ser Ala Glu Lys Asn Phe Trp
1               5                   10                  15

Lys Met Gly Lys Ser Lys Lys Asn Glu Lys Glu Lys Lys Pro
            20                  25                  30

Thr Val Ser Thr Phe Ala Met Phe Arg Tyr Ser Asn Trp Leu Asp Arg
            35                  40                  45

Leu Tyr Met Leu Val Gly Thr Met Ala Ala Ile Ile His Gly Ala Ala
    50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110

Met Thr Thr Tyr Ala Tyr Tyr Tyr Ser Gly Ile Gly Ala Gly Val Leu
        115                 120                 125

Val Ala Ala Tyr Ile Gln Val Ser Phe Trp Cys Leu Ala Ala Gly Arg
130                 135                 140

Gln Ile Leu Lys Ile Arg Lys Gln Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe Gln Ser Ile Ala Thr Phe Phe Thr Gly Phe Ile Val
        195                 200                 205

Gly Phe Thr Arg Gly Trp Lys Leu Thr Leu Val Ile Leu Ala Ile Ser
    210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
        275                 280                 285

Ile Gly Ile Lys Lys Ala Ile Thr Ala Asn Ile Ser Ile Gly Ala Ala
```

-continued

```
              290                 295                 300
Phe Leu Leu Ile Tyr Ala Ser Tyr Ala Leu Ala Phe Trp Tyr Gly Thr
305                 310                 315                 320
Ser Leu Val Leu Ser Ser Glu Tyr Ser Ile Gly Gln Val Leu Thr Val
                325                 330                 335
Phe Phe Ser Val Leu Ile Gly Ala Phe Ser Ile Gly Gln Ala Ser Pro
                340                 345                 350
Ser Ile Glu Ala Phe Ala Asn Ala Arg Gly Ala Ala Tyr Glu Ile Phe
                355                 360                 365
Lys Ile Ile Asp Asn Lys Pro Ser Ile Asp Ser Tyr Ser Lys Ser Gly
370                 375                 380
His Lys Pro Asp Asn Ile Lys Gly Asn Leu Glu Phe Lys Asn Val His
385                 390                 395                 400
Phe Ser Tyr Pro Ser Arg Lys Glu Val Lys Ile Leu Lys Gly Leu Asn
                405                 410                 415
Leu Lys Val Gln Ser Gly Gln Thr Val Ala Leu Val Gly Asn Ser Gly
                420                 425                 430
Cys Gly Lys Ser Thr Thr Val Gln Leu Met Gln Arg Leu Tyr Asp Pro
                435                 440                 445
Thr Asp Gly Met Val Cys Ile Asp Gly Gln Asp Ile Arg Thr Ile Asn
        450                 455                 460
Val Arg His Leu Arg Glu Ile Thr Gly Val Val Ser Gln Glu Pro Val
465                 470                 475                 480
Leu Phe Ala Thr Thr Ile Ala Glu Asn Ile Arg Tyr Gly Arg Glu Asn
                485                 490                 495
Val Thr Met Asp Glu Ile Glu Lys Ala Val Lys Glu Ala Asn Ala Tyr
                500                 505                 510
Asp Phe Ile Met Lys Leu Pro Asn Lys Phe Asp Thr Leu Val Gly Glu
        515                 520                 525
Arg Gly Ala Gln Leu Ser Gly Gln Lys Gln Arg Ile Ala Ile Ala
        530                 535                 540
Arg Ala Leu Val Arg Asn Pro Lys Ile Leu Leu Leu Asp Glu Ala Thr
545                 550                 555                 560
Ser Ala Leu Asp Thr Glu Ser Glu Ala Val Val Gln Val Ala Leu Asp
                565                 570                 575
Lys Ala Arg Lys Gly Arg Thr Thr Ile Val Ile Ala His Arg Leu Ser
                580                 585                 590
Thr Val Arg Asn Ala Asp Val Ile Ala Gly Phe Asp Asp Gly Val Ile
        595                 600                 605
Val Glu Lys Gly Asn His Asp Glu Leu Met Lys Glu Lys Gly Ile Tyr
        610                 615                 620
Phe Lys Leu Val Thr Met Gln Thr Arg Gly Asn Glu Ile Glu Leu Glu
625                 630                 635                 640
Asn Ala Thr Gly Glu Ser Lys Ser Glu Ser Asp Ala Leu Glu Met Ser
                645                 650                 655
Pro Lys Asp Ser Gly Ser Ser Leu Ile Lys Arg Arg Ser Thr Arg Arg
                660                 665                 670
Ser Ile His Ala Pro Gln Gly Gln Asp Arg Lys Leu Gly Thr Lys Glu
                675                 680                 685
Asp Leu Asn Glu Asn Val Pro Pro Val Ser Phe Trp Arg Ile Leu Lys
        690                 695                 700
Leu Asn Ser Thr Glu Trp Pro Tyr Phe Val Val Gly Ile Phe Cys Ala
705                 710                 715                 720
```

-continued

```
Ile Ile Asn Gly Gly Leu Gln Pro Ala Phe Ser Ile Ile Phe Ser Arg
            725                 730                 735

Ile Ile Gly Ile Phe Thr Arg Asp Glu Asp Pro Glu Thr Lys Arg Gln
            740                 745                 750

Asn Ser Asn Met Phe Ser Val Leu Phe Leu Val Leu Gly Ile Ile Ser
            755                 760                 765

Phe Ile Thr Phe Phe Leu Gln Gly Phe Thr Phe Gly Lys Ala Gly Glu
            770                 775                 780

Ile Leu Thr Lys Arg Leu Arg Tyr Met Val Phe Arg Ser Met Leu Arg
785                 790                 795                 800

Gln Asp Val Ser Trp Phe Asp Pro Lys Asn Thr Thr Gly Ala Leu
                    805                 810                 815

Thr Thr Arg Leu Ala Asn Asp Ala Ala Gln Val Lys Gly Ala Ile Gly
                    820                 825                 830

Ser Arg Leu Ala Val Ile Thr Gln Asn Ile Ala Asn Leu Gly Thr Gly
            835                 840                 845

Ile Ile Ile Ser Leu Ile Tyr Gly Trp Gln Leu Thr Leu Leu Leu Leu
850                 855                 860

Ala Ile Val Pro Ile Ile Ala Ile Ala Gly Val Val Glu Met Lys Met
865                 870                 875                 880

Leu Ser Gly Gln Ala Leu Lys Asp Lys Lys Glu Leu Glu Gly Ala Gly
                    885                 890                 895

Lys Ile Ala Thr Glu Ala Ile Glu Asn Phe Arg Thr Val Val Ser Leu
            900                 905                 910

Thr Arg Glu Gln Lys Phe Glu Tyr Met Tyr Ala Gln Ser Leu Gln Val
            915                 920                 925

Pro Tyr Arg Asn Ser Leu Arg Lys Ala His Ile Phe Gly Val Ser Phe
            930                 935                 940

Ser Ile Thr Gln Ala Met Met Tyr Phe Ser Tyr Ala Gly Cys Phe Arg
945                 950                 955                 960

Phe Gly Ala Tyr Leu Val Ala Asn Glu Phe Met Asn Phe Gln Asp Val
                965                 970                 975

Leu Leu Val Phe Ser Ala Ile Val Phe Gly Ala Met Ala Val Gly Gln
            980                 985                 990

Val Ser Ser Phe Ala Pro Asp Tyr Ala Lys Ala Lys Val Ser Ala Ala
            995                 1000                1005

His Val  Ile Met Ile Ile Glu  Lys Ser Pro Leu Ile  Asp Ser Tyr
    1010                1015                1020

Ser Pro  His Gly Leu Lys Pro  Asn Thr Leu Glu Gly  Asn Val Thr
    1025                1030                1035

Phe Asn  Glu Val Val Phe Asn  Tyr Pro Thr Arg Pro  Asp Ile Pro
    1040                1045                1050

Val Leu  Gln Gly Leu Ser Leu  Glu Val Lys Lys Gly  Gln Thr Leu
    1055                1060                1065

Ala Leu  Val Gly Ser Ser Gly  Cys Gly Lys Ser Thr  Val Val Gln
    1070                1075                1080

Leu Leu  Glu Arg Phe Tyr Asp  Pro Leu Ala Gly Ser  Val Leu Ile
    1085                1090                1095

Asp Gly  Lys Glu Ile Lys His  Leu Asn Val Gln Trp  Leu Arg Ala
    1100                1105                1110

His Leu  Gly Ile Val Ser Gln  Glu Pro Ile Leu Phe  Asp Cys Ser
    1115                1120                1125
```

-continued

```
Ile Ala Glu Asn Ile Ala Tyr Gly Asp Asn Ser Arg Val Val Ser
    1130                1135                1140

His Glu Glu Ile Met Gln Ala Ala Lys Glu Ala Asn Ile His His
    1145                1150                1155

Phe Ile Glu Thr Leu Pro Glu Lys Tyr Asn Thr Arg Val Gly Asp
    1160                1165                1170

Lys Gly Thr Gln Leu Ser Gly Gly Gln Lys Gln Arg Ile Ala Ile
    1175                1180                1185

Ala Arg Ala Leu Val Arg Gln Pro His Ile Leu Leu Leu Asp Glu
    1190                1195                1200

Ala Thr Ser Ala Leu Asp Thr Glu Ser Glu Lys Val Val Gln Glu
    1205                1210                1215

Ala Leu Asp Lys Ala Arg Glu Gly Arg Thr Cys Ile Val Ile Ala
    1220                1225                1230

His Arg Leu Ser Thr Ile Gln Asn Ala Asp Leu Ile Val Val Phe
    1235                1240                1245

Gln Asn Gly Lys Val Lys Glu His Gly Thr His Gln Gln Leu Leu
    1250                1255                1260

Ala Gln Lys Gly Ile Tyr Phe Ser Met Val Ser Val Gln Ala Gly
    1265                1270                1275

Ala Lys Arg
    1280

<210> SEQ ID NO 9
<211> LENGTH: 1281
<212> TYPE: PRT
<213> ORGANISM: Canis familiaris

<400> SEQUENCE: 9

Met Asp Pro Glu Gly Gly Arg Lys Gly Ser Ala Glu Lys Asn Phe Trp
1               5                   10                  15

Lys Met Gly Lys Lys Ser Lys Lys Glu Lys Lys Glu Lys Lys Pro
            20                  25                  30

Thr Val Ser Thr Phe Ala Met Phe Arg Tyr Ser Asn Trp Leu Asp Arg
        35                  40                  45

Leu Tyr Met Leu Val Gly Thr Met Ala Ala Ile Ile His Gly Ala Ala
    50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110

Met Thr Thr Tyr Ala Tyr Tyr Ser Gly Ile Gly Ala Gly Val Leu
        115                 120                 125

Val Ala Ala Tyr Ile Gln Val Ser Phe Trp Cys Leu Ala Ala Gly Arg
    130                 135                 140

Gln Ile Leu Lys Ile Arg Lys Gln Phe His Ala Ile Met Arg Gln
145                 150                 155                 160

Glu Ile Gly Trp Phe Asp Val His Asp Val Gly Glu Leu Asn Thr Arg
                165                 170                 175

Leu Thr Asp Asp Val Ser Lys Ile Asn Glu Gly Ile Gly Asp Lys Ile
            180                 185                 190

Gly Met Phe Phe Gln Ser Ile Ala Thr Phe Phe Thr Gly Phe Ile Val
        195                 200                 205
```

-continued

```
Gly Phe Thr Arg Gly Trp Lys Leu Thr Leu Val Ile Leu Ala Ile Ser
210                 215                 220

Pro Val Leu Gly Leu Ser Ala Ala Ile Trp Ala Lys Ile Leu Ser Ser
225                 230                 235                 240

Phe Thr Asp Lys Glu Leu Leu Ala Tyr Ala Lys Ala Gly Ala Val Ala
                245                 250                 255

Glu Glu Val Leu Ala Ala Ile Arg Thr Val Ile Ala Phe Gly Gly Gln
            260                 265                 270

Lys Lys Glu Leu Glu Arg Tyr Asn Lys Asn Leu Glu Glu Ala Lys Gly
        275                 280                 285

Ile Gly Ile Lys Lys Ala Ile Thr Ala Asn Ile Ser Ile Gly Ala Ala
290                 295                 300

Phe Leu Leu Ile Tyr Ala Ser Tyr Ala Leu Ala Phe Trp Tyr Gly Thr
305                 310                 315                 320

Ser Leu Val Leu Ser Ser Glu Tyr Ser Ile Gly Gln Val Leu Thr Val
                325                 330                 335

Phe Phe Ser Val Leu Ile Gly Ala Phe Ser Ile Gly Gln Ala Ser Pro
            340                 345                 350

Ser Ile Glu Ala Phe Ala Asn Ala Arg Gly Ala Ala Tyr Glu Ile Phe
        355                 360                 365

Lys Ile Ile Asp Asn Lys Pro Ser Ile Asp Ser Tyr Ser Lys Ser Gly
370                 375                 380

His Lys Pro Asp Asn Ile Lys Gly Asn Leu Glu Phe Lys Asn Val His
385                 390                 395                 400

Phe Ser Tyr Pro Ser Arg Lys Glu Val Lys Ile Leu Lys Gly Leu Asn
                405                 410                 415

Leu Lys Val Gln Ser Gly Gln Thr Val Ala Leu Val Gly Asn Ser Gly
            420                 425                 430

Cys Gly Lys Ser Thr Thr Val Gln Leu Met Gln Arg Leu Tyr Asp Pro
        435                 440                 445

Thr Asp Gly Met Val Cys Ile Asp Gly Gln Asp Ile Arg Thr Ile Asn
450                 455                 460

Val Arg His Leu Arg Glu Ile Thr Gly Val Val Ser Gln Glu Pro Val
465                 470                 475                 480

Leu Phe Ala Thr Thr Ile Ala Glu Asn Ile Arg Tyr Gly Arg Glu Asn
                485                 490                 495

Val Thr Met Asp Glu Ile Glu Lys Ala Val Lys Glu Ala Asn Ala Tyr
            500                 505                 510

Asp Phe Ile Met Lys Leu Pro Asn Lys Phe Asp Thr Leu Val Gly Glu
        515                 520                 525

Arg Gly Ala Gln Leu Ser Gly Gly Gln Lys Gln Arg Ile Ala Ile Ala
530                 535                 540

Arg Ala Leu Val Arg Asn Pro Lys Ile Leu Leu Leu Asp Glu Ala Thr
545                 550                 555                 560

Ser Ala Leu Asp Thr Glu Ser Glu Ala Val Gln Val Ala Leu Asp
                565                 570                 575

Lys Ala Arg Lys Gly Arg Thr Thr Ile Val Ile Ala His Arg Leu Ser
            580                 585                 590

Thr Val Arg Asn Ala Asp Val Ile Ala Gly Phe Asp Asp Gly Val Ile
        595                 600                 605

Val Glu Lys Gly Asn His Asp Glu Leu Met Lys Glu Lys Gly Ile Tyr
610                 615                 620
```

-continued

```
Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
            645                 650                 655

Pro Lys Asp Ser Gly Ser Ser Leu Ile Lys Arg Arg Ser Thr Arg Arg
            660                 665                 670

Ser Ile His Ala Pro Gln Gly Gln Asp Arg Lys Leu Gly Thr Lys Glu
            675                 680                 685

Asp Leu Asn Glu Asn Val Pro Pro Val Ser Phe Trp Arg Ile Leu Lys
690                 695                 700

Leu Asn Ser Thr Glu Trp Pro Tyr Phe Val Val Gly Ile Phe Cys Ala
705                 710                 715                 720

Ile Ile Asn Gly Gly Leu Gln Pro Ala Phe Ser Ile Ile Phe Ser Arg
            725                 730                 735

Ile Ile Gly Ile Phe Thr Arg Asp Glu Asp Pro Glu Thr Lys Arg Gln
            740                 745                 750

Asn Ser Asn Met Phe Ser Val Leu Phe Leu Val Leu Gly Ile Ile Ser
            755                 760                 765

Phe Ile Thr Phe Leu Gln Gly Phe Thr Phe Gly Lys Ala Gly Glu
770                 775                 780

Ile Leu Thr Lys Arg Leu Arg Tyr Met Val Phe Arg Ser Met Leu Arg
785                 790                 795                 800

Gln Asp Val Ser Trp Phe Asp Asp Pro Lys Asn Thr Thr Gly Ala Leu
                805                 810                 815

Thr Thr Arg Leu Ala Asn Asp Ala Ala Gln Val Lys Gly Ala Ile Gly
                820                 825                 830

Ser Arg Leu Ala Val Ile Thr Gln Asn Ile Ala Asn Leu Gly Thr Gly
            835                 840                 845

Ile Ile Ile Ser Leu Ile Tyr Gly Trp Gln Leu Thr Leu Leu Leu Leu
850                 855                 860

Ala Ile Val Pro Ile Ile Ala Ile Ala Gly Val Val Glu Met Lys Met
865                 870                 875                 880

Leu Ser Gly Gln Ala Leu Lys Asp Lys Lys Glu Leu Glu Gly Ala Gly
                885                 890                 895

Lys Ile Ala Thr Glu Ala Ile Glu Asn Phe Arg Thr Val Val Ser Leu
            900                 905                 910

Thr Arg Glu Gln Lys Phe Glu Tyr Met Tyr Ala Gln Ser Leu Gln Val
            915                 920                 925

Pro Tyr Arg Asn Ser Leu Arg Lys Ala His Ile Phe Gly Val Ser Phe
930                 935                 940

Ser Ile Thr Gln Ala Met Met Tyr Phe Ser Tyr Ala Gly Cys Phe Arg
945                 950                 955                 960

Phe Gly Ala Tyr Leu Val Ala Asn Glu Phe Met Asn Phe Gln Asp Val
            965                 970                 975

Leu Leu Val Phe Ser Ala Ile Val Phe Gly Ala Met Ala Val Gly Gln
            980                 985                 990

Val Ser Ser Phe Ala Pro Asp Tyr Ala Lys Ala Lys Val Ser Ala Ala
            995                 1000                1005

His Val Ile Met Ile Ile Glu Lys Ser Pro Leu Ile Asp Ser Tyr
    1010                1015                1020

Ser Pro His Gly Leu Lys Pro Asn Thr Leu Glu Gly Asn Val Thr
    1025                1030                1035

Phe Asn Glu Val Val Phe Asn Tyr Pro Thr Arg Pro Asp Ile Pro
```

-continued

```
              1040                1045                1050
Val Leu Gln Gly Leu Ser Leu Glu Val Lys Lys Gly Gln Thr Leu
        1055                1060                1065

Ala Leu Val Gly Ser Ser Gly Cys Gly Lys Ser Thr Val Val Gln
        1070                1075                1080

Leu Leu Glu Arg Phe Tyr Asp Pro Leu Ala Gly Ser Val Leu Ile
        1085                1090                1095

Asp Gly Lys Glu Ile Lys His Leu Asn Val Gln Trp Leu Arg Ala
        1100                1105                1110

His Leu Gly Ile Val Ser Gln Glu Pro Ile Leu Phe Asp Cys Ser
        1115                1120                1125

Ile Ala Glu Asn Ile Ala Tyr Gly Asp Asn Ser Arg Val Val Ser
        1130                1135                1140

His Glu Glu Ile Met Gln Ala Ala Lys Glu Ala Asn Ile His His
        1145                1150                1155

Phe Ile Glu Thr Leu Pro Glu Lys Tyr Asn Thr Arg Val Gly Asp
        1160                1165                1170

Lys Gly Thr Gln Leu Ser Gly Gly Gln Lys Gln Arg Ile Ala Ile
        1175                1180                1185

Ala Arg Ala Leu Val Arg Gln Pro His Ile Leu Leu Leu Asp Glu
        1190                1195                1200

Ala Thr Ser Ala Leu Asp Thr Glu Ser Glu Lys Val Val Gln Glu
        1205                1210                1215

Ala Leu Asp Lys Ala Arg Glu Gly Arg Thr Cys Ile Val Ile Ala
        1220                1225                1230

His Arg Leu Ser Thr Ile Gln Asn Ala Asp Leu Ile Val Val Phe
        1235                1240                1245

Gln Asn Gly Lys Val Lys Glu His Gly Thr His Gln Gln Leu Leu
        1250                1255                1260

Ala Gln Lys Gly Ile Tyr Phe Ser Met Val Ser Val Gln Ala Gly
        1265                1270                1275

Ala Lys Arg
        1280

<210> SEQ ID NO 10
<211> LENGTH: 1281
<212> TYPE: PRT
<213> ORGANISM: Canis familiaris

<400> SEQUENCE: 10

Met Asp Pro Glu Gly Gly Arg Lys Gly Ser Ala Glu Lys Asn Phe Trp
1               5                   10                  15

Lys Met Gly Lys Lys Ser Lys Lys Lys Glu Lys Lys Glu Lys Lys Pro
                20                  25                  30

Thr Val Ser Thr Phe Ala Met Phe Arg Tyr Ser Asn Trp Leu Asp Arg
            35                  40                  45

Leu Tyr Met Leu Val Gly Thr Met Ala Ala Ile Ile His Gly Ala Ala
        50                  55                  60

Leu Pro Leu Met Met Leu Val Phe Gly Asn Met Thr Asp Ser Phe Ala
65                  70                  75                  80

Asn Ala Gly Ile Ser Arg Asn Lys Thr Phe Pro Val Ile Ile Asn Glu
                85                  90                  95

Ser Ile Thr Asn Asn Thr Gln His Phe Ile Asn His Leu Glu Glu Glu
            100                 105                 110
```

-continued

```
Met Thr Thr Tyr Ala Tyr Tyr Ser Gly Ile Gly Ala Gly Val Leu
        115                 120                 125
Val Ala Ala Tyr Ile Gln Val Ser Phe Trp Cys Leu Ala Ala Gly Arg
        130                 135                 140
Gln Ile Leu Lys Ile Arg Lys Gln Phe Phe His Ala Ile Met Arg Gln
145                 150                 155                 160
Glu Ile Gly Trp Phe Asp Val His Asp Val Gly Glu Leu Asn Thr Arg
                    165                 170                 175
Leu Thr Asp Asp Val Ser Lys Ile Asn Glu Gly Ile Gly Asp Lys Ile
                180                 185                 190
Gly Met Phe Phe Gln Ser Ile Ala Thr Phe Phe Thr Gly Phe Ile Val
            195                 200                 205
Gly Phe Thr Arg Gly Trp Lys Leu Thr Leu Val Ile Leu Ala Ile Ser
        210                 215                 220
Pro Val Leu Gly Leu Ser Ala Ala Ile Trp Ala Lys Ile Leu Ser Ser
225                 230                 235                 240
Phe Thr Asp Lys Glu Leu Leu Ala Tyr Ala Lys Ala Gly Ala Val Ala
                    245                 250                 255
Glu Glu Val Leu Ala Ala Ile Arg Thr Val Ile Ala Phe Gly Gly Gln
                260                 265                 270
Lys Lys Glu Leu Glu Arg Tyr Asn Lys Asn Leu Glu Glu Ala Lys Gly
            275                 280                 285
Ile Gly Ile Lys Lys Ala Ile Thr Ala Asn Ile Ser Ile Gly Ala Ala
        290                 295                 300
Phe Leu Leu Ile Tyr Ala Ser Tyr Ala Leu Ala Phe Trp Tyr Gly Thr
305                 310                 315                 320
Ser Leu Val Leu Ser Ser Glu Tyr Thr Ile Gly Gln Val Leu Thr Val
                    325                 330                 335
Phe Phe Ser Val Leu Ile Gly Ala Phe Ser Ile Gly Gln Ala Ser Pro
                340                 345                 350
Ser Ile Glu Ala Phe Ala Asn Ala Arg Gly Ala Ala Tyr Glu Ile Phe
            355                 360                 365
Lys Ile Ile Asp Asn Lys Pro Ser Ile Asp Ser Tyr Ser Lys Ser Gly
        370                 375                 380
His Lys Pro Asp Asn Ile Lys Gly Asn Leu Glu Phe Lys Asn Val His
385                 390                 395                 400
Phe Ser Tyr Pro Ser Arg Lys Glu Val Lys Ile Leu Lys Gly Leu Asn
                    405                 410                 415
Leu Lys Val Gln Ser Gly Gln Thr Val Ala Leu Val Gly Asn Ser Gly
                420                 425                 430
Cys Gly Lys Ser Thr Thr Val Gln Leu Met Gln Arg Leu Tyr Asp Pro
            435                 440                 445
Thr Asp Gly Met Val Cys Ile Asp Gly Gln Asp Ile Arg Thr Ile Asn
        450                 455                 460
Val Arg His Leu Arg Glu Ile Thr Gly Val Val Ser Gln Glu Pro Val
465                 470                 475                 480
Leu Phe Ala Thr Thr Ile Ala Glu Asn Ile Arg Tyr Gly Arg Glu Asn
                    485                 490                 495
Val Thr Met Asp Glu Ile Glu Lys Ala Val Lys Glu Ala Asn Ala Tyr
                500                 505                 510
Asp Phe Ile Met Lys Leu Pro Asn Lys Phe Asp Thr Leu Val Gly Glu
            515                 520                 525
Arg Gly Ala Gln Leu Ser Gly Gly Gln Lys Gln Arg Ile Ala Ile Ala
```

-continued

```
            530                 535                 540
Arg Ala Leu Val Arg Asn Pro Lys Ile Leu Leu Asp Glu Ala Thr
545                 550                 555                 560

Ser Ala Leu Asp Thr Glu Ser Glu Ala Val Val Gln Val Ala Leu Asp
                565                 570                 575

Lys Ala Arg Lys Gly Arg Thr Thr Ile Val Ile Ala His Arg Leu Ser
                580                 585                 590

Thr Val Arg Asn Ala Asp Val Ile Ala Gly Phe Asp Asp Gly Val Ile
                595                 600                 605

Val Glu Lys Gly Asn His Asp Glu Leu Met Lys Glu Lys Gly Ile Tyr
            610                 615                 620

Phe Lys Leu Val Thr Met Gln Thr Arg Gly Asn Glu Ile Glu Leu Glu
625                 630                 635                 640

Asn Ala Thr Gly Glu Ser Lys Ser Glu Ser Asp Ala Leu Glu Met Ser
                645                 650                 655

Pro Lys Asp Ser Gly Ser Ser Leu Ile Lys Arg Arg Ser Thr Arg Arg
                660                 665                 670

Ser Ile His Ala Pro Gln Gly Gln Asp Arg Lys Leu Gly Thr Lys Glu
                675                 680                 685

Asp Leu Asn Glu Asn Val Pro Pro Val Ser Phe Trp Arg Ile Leu Lys
            690                 695                 700

Leu Asn Ser Thr Glu Trp Pro Tyr Phe Val Val Gly Ile Phe Cys Ala
705                 710                 715                 720

Ile Ile Asn Gly Gly Leu Gln Pro Ala Phe Ser Ile Ile Phe Ser Arg
                725                 730                 735

Ile Ile Gly Ile Phe Thr Arg Asp Glu Asp Pro Glu Thr Lys Arg Gln
                740                 745                 750

Asn Ser Asn Met Phe Ser Val Leu Phe Leu Val Leu Gly Ile Ile Ser
                755                 760                 765

Phe Ile Thr Phe Phe Leu Gln Gly Phe Thr Phe Gly Lys Ala Gly Glu
                770                 775                 780

Ile Leu Thr Lys Arg Leu Arg Tyr Met Val Phe Arg Ser Met Leu Arg
785                 790                 795                 800

Gln Asp Val Ser Trp Phe Asp Asp Pro Lys Asn Thr Thr Gly Ala Leu
                805                 810                 815

Thr Thr Arg Leu Ala Asn Asp Ala Ala Gln Val Lys Gly Ala Ile Gly
                820                 825                 830

Ser Arg Leu Ala Val Ile Thr Gln Asn Ile Ala Asn Leu Gly Thr Gly
                835                 840                 845

Ile Ile Ile Ser Leu Ile Tyr Gly Trp Gln Leu Thr Leu Leu Leu Leu
            850                 855                 860

Ala Ile Val Pro Ile Ile Ala Ile Ala Gly Val Val Glu Met Lys Met
865                 870                 875                 880

Leu Ser Gly Gln Ala Leu Lys Asp Lys Lys Glu Leu Glu Gly Ala Gly
                885                 890                 895

Lys Ile Ala Thr Glu Ala Ile Glu Asn Phe Arg Thr Val Val Ser Leu
                900                 905                 910

Thr Arg Glu Gln Lys Phe Glu Tyr Met Tyr Ala Gln Ser Leu Gln Val
                915                 920                 925

Pro Tyr Arg Asn Ser Leu Arg Lys Ala His Ile Phe Gly Val Ser Phe
            930                 935                 940

Ser Ile Thr Gln Ala Met Met Tyr Phe Ser Tyr Ala Gly Cys Phe Arg
945                 950                 955                 960
```

```
Phe Gly Ala Tyr Leu Val Ala Asn Glu Phe Met Asn Phe Gln Asp Val
                965                 970                 975

Leu Leu Val Phe Ser Ala Ile Val Phe Gly Ala Met Ala Val Gly Gln
            980                 985                 990

Val Ser Ser Phe Ala Pro Asp Tyr Ala Lys Ala Lys Val Ser Ala Ala
        995                1000                1005

His Val Ile Met Ile Ile Glu Lys Ser Pro Leu Ile Asp Ser Tyr
    1010                1015                1020

Ser Pro His Gly Leu Lys Pro Asn Thr Leu Glu Gly Asn Val Thr
    1025                1030                1035

Phe Asn Glu Val Val Phe Asn Tyr Pro Thr Arg Pro Asp Ile Pro
    1040                1045                1050

Val Leu Gln Gly Leu Ser Leu Glu Val Lys Lys Gly Gln Thr Leu
    1055                1060                1065

Ala Leu Val Gly Ser Ser Gly Cys Gly Lys Ser Thr Val Val Gln
    1070                1075                1080

Leu Leu Glu Arg Phe Tyr Asp Pro Leu Ala Gly Ser Val Leu Ile
    1085                1090                1095

Asp Gly Lys Glu Ile Lys His Leu Asn Val Gln Trp Leu Arg Ala
    1100                1105                1110

His Leu Gly Ile Val Ser Gln Glu Pro Ile Leu Phe Asp Cys Ser
    1115                1120                1125

Ile Ala Glu Asn Ile Ala Tyr Gly Asp Asn Ser Arg Val Val Ser
    1130                1135                1140

His Glu Glu Ile Val Gln Ala Ala Lys Glu Ala Asn Ile His His
    1145                1150                1155

Phe Ile Glu Thr Leu Pro Glu Lys Tyr Asn Thr Arg Val Gly Asp
    1160                1165                1170

Lys Gly Thr Gln Leu Ser Gly Gly Gln Lys Gln Arg Ile Ala Ile
    1175                1180                1185

Ala Arg Ala Leu Val Arg Gln Pro His Ile Leu Leu Asp Glu
    1190                1195                1200

Ala Thr Ser Ala Leu Asp Thr Glu Ser Glu Lys Val Val Gln Glu
    1205                1210                1215

Ala Leu Asp Lys Ala Arg Glu Gly Arg Thr Cys Ile Val Ile Ala
    1220                1225                1230

His Arg Leu Ser Thr Ile Gln Asn Ala Asp Leu Ile Val Val Phe
    1235                1240                1245

Gln Asn Gly Lys Val Lys Glu His Gly Thr His Gln Gln Leu Leu
    1250                1255                1260

Ala Gln Lys Gly Ile Tyr Phe Ser Met Val Ser Val Gln Ala Gly
    1265                1270                1275

Ala Lys Arg
    1280

<210> SEQ ID NO 11
<211> LENGTH: 1280
<212> TYPE: PRT
<213> ORGANISM: Canis familiaris

<400> SEQUENCE: 11

Met Asp Pro Glu Gly Gly Arg Lys Gly Ser Ala Glu Lys Asn Phe Trp
1               5                   10                  15

Lys Met Gly Lys Lys Ser Lys Lys Glu Lys Lys Glu Lys Lys Pro Thr
```

-continued

```
            20                  25                  30
Val Ser Thr Phe Ala Met Phe Arg Tyr Ser Asn Trp Leu Asp Arg Leu
        35                  40                  45

Tyr Met Leu Val Gly Thr Met Ala Ala Ile Ile His Gly Ala Ala Leu
        50                  55                  60

Pro Leu Met Met Leu Val Phe Gly Asn Met Thr Asp Ser Phe Ala Asn
 65                  70                  75                  80

Ala Gly Ile Ser Arg Asn Lys Thr Phe Pro Val Ile Ile Asn Glu Ser
                85                  90                  95

Ile Thr Asn Asn Thr Gln His Phe Ile Asn His Leu Glu Glu Glu Met
            100                 105                 110

Thr Thr Tyr Ala Tyr Tyr Ser Gly Ile Gly Ala Gly Val Leu Val
            115                 120                 125

Ala Ala Tyr Ile Gln Val Ser Phe Trp Cys Leu Ala Ala Gly Arg Gln
            130                 135                 140

Ile Leu Lys Ile Arg Lys Gln Phe Phe His Ala Ile Met Arg Gln Glu
145                 150                 155                 160

Ile Gly Trp Phe Asp Val His Asp Val Gly Glu Leu Asn Thr Arg Leu
                165                 170                 175

Thr Asp Asp Val Ser Lys Ile Asn Glu Gly Ile Gly Asp Lys Val Gly
            180                 185                 190

Met Phe Phe Gln Ser Ile Ala Thr Phe Phe Thr Gly Phe Ile Val Gly
            195                 200                 205

Phe Thr Pro Gly Trp Lys Leu Thr Leu Val Ile Leu Ala Ile Ser Pro
            210                 215                 220

Val Leu Gly Leu Ser Ala Ala Ile Trp Ala Lys Ile Leu Ser Ser Phe
225                 230                 235                 240

Thr Asp Lys Glu Leu Leu Ala Tyr Ala Lys Ala Gly Ala Val Ala Glu
                245                 250                 255

Glu Val Leu Ala Ala Ile Arg Thr Val Ile Ala Phe Gly Gly Gln Lys
            260                 265                 270

Lys Glu Leu Glu Arg Tyr Asn Lys Asn Leu Glu Glu Ala Lys Arg Ile
            275                 280                 285

Gly Ile Lys Lys Ala Ile Thr Ala Asn Ile Ser Ile Gly Ala Ala Phe
            290                 295                 300

Leu Leu Ile Tyr Ala Ser Tyr Ala Leu Ala Phe Trp Tyr Gly Thr Ser
305                 310                 315                 320

Leu Val Leu Ser Ser Glu Tyr Thr Ile Gly Gln Val Leu Thr Val Phe
                325                 330                 335

Phe Ser Val Leu Ile Gly Ala Phe Ser Ile Gly Gln Ala Ser Pro Ser
            340                 345                 350

Ile Glu Ala Phe Ala Asn Ala Arg Gly Ala Ala Tyr Glu Ile Phe Lys
            355                 360                 365

Ile Ile Asp Asn Lys Pro Ser Ile Asp Ser Tyr Ser Lys Ser Gly His
            370                 375                 380

Lys Pro Asp Asn Ile Lys Gly Asn Leu Glu Phe Lys Asn Val His Phe
385                 390                 395                 400

Ser Tyr Pro Ser Arg Lys Glu Val Lys Ile Leu Lys Gly Leu Asn Leu
                405                 410                 415

Lys Val Gln Ser Gly Gln Thr Val Ala Leu Val Gly Asn Ser Gly Cys
            420                 425                 430

Gly Lys Ser Thr Thr Val Gln Leu Met Gln Arg Leu Tyr Asp Pro Thr
            435                 440                 445
```

```
                    -continued

Asp Gly Met Val Cys Ile Asp Gly Gln Asp Ile Arg Thr Ile Asn Val
            450                 455                 460

Arg His Leu Arg Glu Ile Thr Gly Val Val Ser Gln Glu Pro Val Leu
465                 470                 475                 480

Phe Ala Thr Thr Ile Ala Glu Asn Ile Arg Tyr Gly Arg Glu Asn Val
                        485                 490                 495

Thr Met Asp Glu Ile Glu Lys Ala Val Lys Glu Ala Asn Ala Tyr Asp
                500                 505                 510

Phe Ile Met Lys Leu Pro Asn Lys Phe Asp Thr Leu Val Gly Glu Arg
            515                 520                 525

Gly Ala Arg Leu Ser Gly Gln Lys Gln Arg Ile Ala Ile Ala Arg
        530                 535                 540

Ala Leu Val Arg Asn Pro Lys Ile Leu Leu Leu Asp Glu Ala Thr Ser
545                 550                 555                 560

Ala Leu Asp Thr Glu Ser Glu Ala Val Val Gln Val Ala Leu Asp Lys
                        565                 570                 575

Ala Arg Lys Gly Arg Thr Thr Ile Val Ile Ala His Arg Leu Ser Thr
                580                 585                 590

Val Arg Asn Ala Asp Val Ile Ala Gly Phe Asp Asp Gly Val Ile Val
            595                 600                 605

Glu Lys Gly Asn His Asp Glu Leu Met Lys Glu Lys Gly Ile Tyr Phe
        610                 615                 620

Lys Leu Val Thr Met Gln Thr Arg Gly Asn Glu Ile Glu Leu Glu Asn
625                 630                 635                 640

Ala Thr Gly Glu Ser Lys Ser Glu Ser Asp Ala Leu Glu Met Ser Pro
                        645                 650                 655

Lys Asp Ser Gly Ser Ser Leu Ile Lys Arg Arg Ser Thr Arg Arg Ser
                660                 665                 670

Ile His Ala Pro Gln Gly Gln Asp Arg Lys Leu Gly Thr Lys Glu Asp
            675                 680                 685

Leu Asn Glu Asn Val Pro Ser Val Ser Phe Trp Arg Ile Leu Lys Leu
        690                 695                 700

Asn Ser Thr Glu Trp Pro Tyr Phe Val Val Gly Ile Phe Cys Ala Ile
705                 710                 715                 720

Ile Asn Gly Gly Leu Gln Pro Ala Phe Ser Ile Phe Ser Arg Ile
                        725                 730                 735

Ile Gly Ile Phe Thr Arg Asp Glu Asp Pro Glu Thr Lys Arg Gln Asn
                740                 745                 750

Ser Asn Met Phe Ser Val Leu Phe Leu Val Leu Gly Ile Ile Ser Phe
            755                 760                 765

Ile Thr Phe Phe Leu Gln Gly Phe Thr Phe Gly Lys Ala Gly Glu Ile
        770                 775                 780

Leu Thr Lys Arg Leu Arg Tyr Met Val Phe Arg Ser Met Leu Arg Gln
785                 790                 795                 800

Asp Val Ser Trp Phe Asp Asp Pro Lys Asn Thr Thr Gly Ala Leu Thr
                        805                 810                 815

Thr Arg Leu Ala Asn Asp Ala Ala Gln Val Lys Gly Ala Ile Gly Ser
                820                 825                 830

Arg Leu Ala Val Ile Thr Gln Asn Ile Ala Asn Leu Gly Thr Gly Ile
            835                 840                 845

Ile Ile Ser Leu Ile Tyr Gly Trp Gln Leu Thr Leu Leu Leu Leu Ala
        850                 855                 860
```

-continued

```
Ile Val Pro Ile Ile Ala Ile Ala Gly Val Val Glu Met Lys Met Leu
865                 870                 875                 880

Ser Gly Gln Ala Leu Lys Asp Lys Lys Glu Leu Gly Ala Gly Lys
                885                 890                 895

Ile Ala Thr Glu Ala Ile Glu Asn Phe Arg Thr Val Val Ser Leu Thr
                900                 905                 910

Arg Glu Gln Lys Phe Glu Tyr Met Tyr Ala Gln Ser Leu Gln Val Pro
            915                 920                 925

Tyr Arg Asn Ser Leu Arg Lys Ala His Ile Phe Gly Val Ser Phe Ser
    930                 935                 940

Ile Thr Gln Ala Met Met Tyr Phe Ser Tyr Ala Gly Cys Phe Arg Phe
945                 950                 955                 960

Gly Ala Tyr Leu Val Ala Asn Glu Phe Met Asn Phe Gln Asp Val Leu
                965                 970                 975

Leu Val Phe Ser Ala Ile Val Phe Gly Ala Met Ala Val Gly Gln Val
                980                 985                 990

Ser Ser Phe Ala Pro Asp Tyr Ala  Lys Ala Lys Val Ser  Ala Ala His
        995                 1000                1005

Val Ile  Met Ile Ile Glu Lys  Ser Pro Leu Ile Asp  Ser Tyr Ser
    1010                1015                1020

Pro His  Gly Leu Lys Pro Asn  Thr Leu Glu Gly Asn  Val Thr Phe
    1025                1030                1035

Asn Glu  Val Val Phe Asn Tyr  Pro Thr Arg Pro Asp  Ile Pro Val
    1040                1045                1050

Leu Gln  Gly Leu Ser Leu Glu  Val Lys Lys Gly Gln  Thr Leu Ala
    1055                1060                1065

Leu Val  Gly Ser Ser Gly Cys  Gly Lys Ser Thr Val  Val Gln Leu
    1070                1075                1080

Leu Glu  Arg Phe Tyr Asp Pro  Leu Ala Gly Ser Val  Leu Ile Asp
    1085                1090                1095

Gly Lys  Glu Ile Lys His Leu  Asn Val Gln Trp Leu  Arg Ala His
    1100                1105                1110

Leu Gly  Ile Val Ser Gln Glu  Pro Ile Leu Phe Asp  Cys Ser Ile
    1115                1120                1125

Ala Glu  Asn Ile Ala Tyr Gly  Asp Asn Ser Arg Val  Val Ser His
    1130                1135                1140

Glu Glu  Ile Met Gln Ala Ala  Lys Glu Ala Asn Ile  His His Phe
    1145                1150                1155

Ile Glu  Thr Leu Pro Glu Lys  Tyr Asn Thr Arg Val  Gly Asp Lys
    1160                1165                1170

Gly Thr  Gln Leu Ser Gly Gly  Gln Lys Gln Arg Ile  Ala Ile Ala
    1175                1180                1185

Arg Ala  Leu Val Arg Gln Pro  His Ile Leu Leu Leu  Asp Glu Ala
    1190                1195                1200

Thr Ser  Ala Leu Asp Thr Glu  Ser Glu Lys Val Val  Gln Glu Ala
    1205                1210                1215

Leu Asp  Lys Ala Arg Glu Gly  Arg Thr Cys Ile Val  Ile Ala His
    1220                1225                1230

Arg Leu  Ser Thr Ile Gln Asn  Ala Asp Leu Ile Val  Val Phe Gln
    1235                1240                1245

Asn Gly  Lys Val Lys Glu His  Gly Thr His Gln Gln  Leu Leu Ala
    1250                1255                1260

Gln Lys  Gly Ile Tyr Phe Ser  Met Ile Ser Val Gln  Ala Gly Ala
```

```
           1265                1270                1275
Lys Arg
     1280
```

<210> SEQ ID NO 12
<211> LENGTH: 27
<212> TYPE: DNA
<213> ORGANISM: Homo sapiens

<400> SEQUENCE: 12
ctggacttcc tctcatgatg ctggtgt                                            27

<210> SEQ ID NO 13
<211> LENGTH: 28
<212> TYPE: DNA
<213> ORGANISM: Artificial Sequence
<220> FEATURE:
<223> OTHER INFORMATION: T7 primer based on Stratagene sequence

<400> SEQUENCE: 13
ttgtaatacg actcactata gggcgaat                                           28

<210> SEQ ID NO 14
<211> LENGTH: 28
<212> TYPE: DNA
<213> ORGANISM: Artificial Sequence
<220> FEATURE:
<223> OTHER INFORMATION: Primer based on Macaca fascicularis and Homo
      sapiens PGP

<400> SEQUENCE: 14
cttttcgaga tgggtaactg aagtgaac                                           28

<210> SEQ ID NO 15
<211> LENGTH: 28
<212> TYPE: DNA
<213> ORGANISM: Artificial Sequence
<220> FEATURE:
<223> OTHER INFORMATION: Primer based on Macaca fascicularis and Homo
      sapiens PGP

<400> SEQUENCE: 15
agaaggtgct gggaagatcg ctactgaa                                           28

<210> SEQ ID NO 16
<211> LENGTH: 30
<212> TYPE: DNA
<213> ORGANISM: Artificial Sequence
<220> FEATURE:
<223> OTHER INFORMATION: Primer based on Macaca fascicularis and Homo
      sapiens PGP

<400> SEQUENCE: 16
catatcttcc tccagattca tgacgggcac                                         30

<210> SEQ ID NO 17
<211> LENGTH: 27
<212> TYPE: DNA
<213> ORGANISM: Artificial Sequence
<220> FEATURE:
<223> OTHER INFORMATION: T3 primer based on Stratagene sequence

<400> SEQUENCE: 17
aagctcgaaa ttaaccctca ctaaagg                                            27

```
<210> SEQ ID NO 18
<211> LENGTH: 21
<212> TYPE: DNA
<213> ORGANISM: Macaca fascicularis

<400> SEQUENCE: 18
cgctggtttc gatgatggag t                                        21

<210> SEQ ID NO 19
<211> LENGTH: 24
<212> TYPE: DNA
<213> ORGANISM: Macaca fascicularis

<400> SEQUENCE: 19
cagtcgggtg ggatagttga atac                                     24

<210> SEQ ID NO 20
<211> LENGTH: 25
<212> TYPE: DNA
<213> ORGANISM: Macaca fascicularis

<400> SEQUENCE: 20
gccaatattt ctataggtgc tgctt                                    25

<210> SEQ ID NO 21
<211> LENGTH: 25
<212> TYPE: DNA
<213> ORGANISM: Macaca fascicularis

<400> SEQUENCE: 21
ggtatacttt catccagagc ctctt                                    25

<210> SEQ ID NO 22
<211> LENGTH: 16
<212> TYPE: DNA
<213> ORGANISM: Artificial Sequence
<220> FEATURE:
<223> OTHER INFORMATION: M13F primer based on Invitrogen sequence

<400> SEQUENCE: 22
gtaaaacgac ggccag                                              16

<210> SEQ ID NO 23
<211> LENGTH: 17
<212> TYPE: DNA
<213> ORGANISM: Artificial Sequence
<220> FEATURE:
<223> OTHER INFORMATION: M13R primer based on Invitrogen sequence

<400> SEQUENCE: 23
caggaaacag ctatgac                                             17

<210> SEQ ID NO 24
<211> LENGTH: 28
<212> TYPE: DNA
<213> ORGANISM: Artificial Sequence
<220> FEATURE:
<223> OTHER INFORMATION: Primer based on Macaca fascicularis and Homo
      sapiens PGP

<400> SEQUENCE: 24
agaaggtgct gggaagatcg ctactgaa                                 28

<210> SEQ ID NO 25
<211> LENGTH: 18
```

```
<212> TYPE: DNA
<213> ORGANISM: Macaca fascicularis

<400> SEQUENCE: 25
gcctaaagcc gaacacat                                                    18

<210> SEQ ID NO 26
<211> LENGTH: 24
<212> TYPE: DNA
<213> ORGANISM: Macaca fascicularis

<400> SEQUENCE: 26
ttatgctctg gccttctggt atgg                                             24

<210> SEQ ID NO 27
<211> LENGTH: 26
<212> TYPE: DNA
<213> ORGANISM: Macaca fascicularis

<400> SEQUENCE: 27
ttgtttcggc atcatcattt cttgta                                           26

<210> SEQ ID NO 28
<211> LENGTH: 21
<212> TYPE: DNA
<213> ORGANISM: Macaca fascicularis

<400> SEQUENCE: 28
cgctggtttc gatgatggag t                                                21

<210> SEQ ID NO 29
<211> LENGTH: 23
<212> TYPE: DNA
<213> ORGANISM: Macaca fascicularis

<400> SEQUENCE: 29
gctttaggcc ttctgtgctg tag                                              23

<210> SEQ ID NO 30
<211> LENGTH: 20
<212> TYPE: DNA
<213> ORGANISM: Macaca mulatta

<400> SEQUENCE: 30
gccaattata cacgccttca                                                  20

<210> SEQ ID NO 31
<211> LENGTH: 18
<212> TYPE: DNA
<213> ORGANISM: Macaca mulatta

<400> SEQUENCE: 31
cgcaatggag gagcagag                                                    18

<210> SEQ ID NO 32
<211> LENGTH: 20
<212> TYPE: DNA
<213> ORGANISM: Macaca mulatta

<400> SEQUENCE: 32
tcgaatagct gtcaatactt                                                  20

<210> SEQ ID NO 33
```

```
<211> LENGTH: 25
<212> TYPE: DNA
<213> ORGANISM: Macaca fascicularis

<400> SEQUENCE: 33
cagacctcca tttataatgg cacaa                                              25

<210> SEQ ID NO 34
<211> LENGTH: 25
<212> TYPE: DNA
<213> ORGANISM: Macaca fascicularis

<400> SEQUENCE: 34
gctcatcgtt tgtctacggt tcgta                                              25

<210> SEQ ID NO 35
<211> LENGTH: 12
<212> TYPE: DNA
<213> ORGANISM: Macaca mulatta

<400> SEQUENCE: 35
gtattttaag ct                                                            12

<210> SEQ ID NO 36
<211> LENGTH: 12
<212> TYPE: DNA
<213> ORGANISM: Macaca mulatta

<400> SEQUENCE: 36
gtattttcag ct                                                            12

<210> SEQ ID NO 37
<211> LENGTH: 15
<212> TYPE: DNA
<213> ORGANISM: Macaca mulatta

<400> SEQUENCE: 37
ttcaatgttc gctat                                                         15

<210> SEQ ID NO 38
<211> LENGTH: 16
<212> TYPE: DNA
<213> ORGANISM: Macaca mulatta

<400> SEQUENCE: 38
ttcaatgttt cgctat                                                        16
```